United States Patent [19]

Lundgren

[11] Patent Number: 5,700,479
[45] Date of Patent: Dec. 23, 1997

[54] SURGICAL ELEMENT AND METHOD FOR SELECTIVE TISSUE REGENERATION

[75] Inventor: Dan Lundgren, Hovas, Sweden

[73] Assignee: Guidor AB, Huddinge, Sweden

[21] Appl. No.: 337,652

[22] Filed: Nov. 10, 1994

Related U.S. Application Data

[63] Continuation of Ser. No. 926,604, Aug. 5, 1992, abandoned, which is a continuation-in-part of Ser. No. 689,236, filed as PCT/SE89/00746, Dec. 22, 1989, abandoned.

[30] Foreign Application Priority Data

Dec. 23, 1988 [SE] Sweden ............... 88/04641

[51] Int. Cl.$^6$ .................. A61K 6/00; A61C 13/00
[52] U.S. Cl. .......... 424/435; 424/422; 424/423; 424/426; 623/11
[58] Field of Search .................. 424/401, 422, 424/423, 426, 435; 623/11

[56] References Cited

U.S. PATENT DOCUMENTS

| | | | |
|---|---|---|---|
| 2,991,224 | 7/1961 | Bell | 16/60 |
| 3,386,440 | 6/1968 | Cohen | 128/260 |
| 3,739,773 | 6/1973 | Schmitt et al. | 128/92 |
| 3,754,332 | 8/1973 | Warren, Jr. | 32/64 |
| 3,887,699 | 6/1975 | Yolles | 424/19 |
| 3,953,566 | 4/1976 | Gore | 264/288 |
| 4,020,558 | 5/1977 | Cournut et al. | 32/40 |
| 4,039,653 | 8/1977 | DeFoney et al. | 424/19 |
| 4,136,162 | 1/1979 | Fuchs et al. | 424/27 |
| 4,175,326 | 11/1979 | Goodson | 433/80 |
| 4,186,448 | 2/1980 | Brekke | 3/1.9 |
| 4,244,689 | 1/1981 | Ashman | 433/175 |
| 4,309,776 | 1/1982 | Berguer | 3/1 |
| 4,321,914 | 3/1982 | Begovac et al. | 128/1 |
| 4,407,787 | 10/1983 | Stemberger | 424/28 |
| 4,453,939 | 6/1984 | Zimmerman et al. | 604/368 |
| 4,492,577 | 1/1985 | Farris et al. | 433/201 |
| 4,500,676 | 2/1985 | Balazs et al. | 525/54.2 |
| 4,531,916 | 7/1985 | Scantlebury et al. | 433/173 |
| 4,568,535 | 2/1986 | Loesche | 424/19 |
| 4,599,084 | 7/1986 | Nashef | 623/16 |
| 4,655,980 | 4/1987 | Chu | 264/102 |
| 4,675,381 | 6/1987 | Bichon | 530/345 |
| 4,702,917 | 10/1987 | Schindler | 424/422 |

(List continued on next page.)

FOREIGN PATENT DOCUMENTS

| | | |
|---|---|---|
| 0089782 | 9/1983 | European Pat. Off. |
| 1390445 | 4/1975 | United Kingdom. |
| 1602932 | 11/1981 | United Kingdom. |
| WO88/04557 | 6/1988 | WIPO. |
| WO 90/07308 | 7/1990 | WIPO. |
| WO 90/11730 | 10/1990 | WIPO. |
| WO 91/14404 | 10/1991 | WIPO. |

OTHER PUBLICATIONS

Andreasen, "Interrelation between Alveolar Bone and Periodontal Ligament Repair after Replantation of Mature Permanent Incisors in Monkeys," Journal of Periodontal Research, 1981, vol. 16, pp. 228–235.

Aukhil et al., "An Experimental of New Attachment Procedure in Beagle Dogs," Journal of Periodontal Research, 1983, vol. 18, pp. 643–654.

(List continued on next page.)

*Primary Examiner*—Sally Gardner-Lane
*Attorney, Agent, or Firm*—Kenyon & Kenyon

[57] ABSTRACT

A surgical element for guided and controlled tissue regeneration and method for selective tissue regeneration. The elements disclosed include embodiments containing protrusions on at least one side of a sheet of element material for separating the implanted element from an adjacent surface, and other embodiments comprising multiple layers of element material with internal spacer means separating the layers. Also disclosed is a method for treating supporting tissues adjacent to teeth and dental implants, the method comprising the use of a surgical element for selected influence on the growth of alveolar bone and periodontal ligament tissues.

26 Claims, 16 Drawing Sheets

U.S. PATENT DOCUMENTS

| | | | |
|---|---|---|---|
| 4,752,294 | 6/1988 | Lundgren | 623/11 |
| 4,828,563 | 5/1989 | Müller-Lierheim | 623/16 |
| 4,851,521 | 7/1989 | della Valle et al. | |
| 4,853,225 | 8/1989 | Wahlig et al. | 424/423 |
| 4,861,268 | 8/1989 | Garay et al. | 433/229 |
| 4,876,092 | 10/1989 | Mizobuchi et al. | 424/435 |
| 4,892,736 | 1/1990 | Goodson | 424/435 |
| 4,894,231 | 1/1990 | Moreau et al. | 424/426 |
| 4,976,962 | 12/1990 | Bichon et al. | 424/424 |
| 5,013,553 | 5/1991 | Southard et al. | 424/426 |
| 5,032,445 | 7/1991 | Scantlebury et al. | 428/158 |

OTHER PUBLICATIONS

Boyko et al., "Formation of New Periodontal Ligament by Periodontal Ligament Cells Implanted in Vivo After Culture in Vitro," Journal of Periodontal Research, 1981, vol. 16, pp. 73–88.

Buser et al., "Regeneration and Enlargement of Jaw Bone Using Guided Tissue Regeneration," Clin. Oral. Impl. Res., 1990, vol. 1, pp. 22–32.

Caton and Nyman, "Histometric Evaluation of Periodontal Surgery. I. The Modified Widman Flap Procedure," Journal of Clinical Peridontology, 1980, vol. 7, pp. 212–223.

Caton et al., "Histometric Evaluation of Periodontal Surgery. II. Connective Tissue Attachment Levels After Four Regenerative Procedures," Journal of Clinical Periodontology, 1980, vol. 7, pp. 224–231.

Caton et al., "Periodontal Regeneration via Selective Cell Repopulation," Journal of Periodontology, 1987, vol. 58, pp. 546–552.

Dahlin et al., "Generation of New Bone Around Titanium Implants Using a Membrane Technique: An Experimental Study in Rabbits," The International Journal of Oral & Maxillofacial Implants, 1989, vol. 4, No. 1, pp. 19–25.

Dahlin et al., "Healing of Bone Defects by Guided Tissue Regeneration," Plastic and Reconstructive Surgery, May 1988, vol. 81, No. 5, pp. 672–676.

Dahlin et al., "Healing of Maxillary and Mandibular Bone Defects Using a Membrane Technique," Scand. J. Plast. Reconstr. Hand Surg., 1990, vol. 24, pp. 13–19.

Ellegaard et al., "New Periodontal Attachment Procedure Based on Retardation of Epithelial Migration," Journal of Periodontology, Jan. 1974, vol. 1, pp. 75–88.

Gottlow et al., "Guided Tissue Regeneration Following Treatment of Recession–Type Defects in the Monkey," J. Periodontol., 1990, vol. 61, pp. 680–685.

Gottlow et al., "New Attachment Formation as the Result of Controlled Tissue Regeneration," Journal of Clinical Periodontology, 1984, vol. 11, pp. 494–503.

Gottlow et al., "New Attachment Formation in the Human Periodontium by Guided Tissue Regeneration," J. Clin. Periodontol., 1986, vol. 13, pp. 604–616.

Gottlow et al., "Treatment of Localized Gingival Recessions with Coronally Displaced Flaps and Citric Acid," J. Clin. Periodontol., 1986, vol. 13, pp. 57–63.

Greaves et al., "Malignant Fibrous Histiocytoma in Rats at Sites of Implanted Millipore Filters," American Journal of Pathology, Aug. 1985, vol. 120, pp. 207–214.

Houston et al., "Healing After Root Reimplantation in the Monkey," Journal of Clinical Periodontology, 1985, vol. 12, pp. 716–727.

Isidor et al., "New Attachment Formation on Citric Acid Treated Roots," Journal of Periodontal Research, 1985, vol. 20, pp. 421–430.

Isidor et al., "New Attachment—Reattachment Following Reconstructive Periodontal Surgery," Journal of Clinical Periodontology, 1985, vol. 12, pp. 728–735.

Isidor et al., "The Significance of Coronal Growth of Periodontal Ligament Tissue for New Attachment Formation," J. Clin. Periodontol., 1986, vol. 13, pp. 145–150.

Karring et al., "Bone Regeneration in Orthodontically Produced Alveolar Bone Dehiscences," Journal of Periodontal Research, 1982, vol. 17, pp. 309–318.

Karring et al., "Healing Following Implantation of Periodontitis Affected Roots into Bone Tissue," Journal of Clinical Periodontology, 1980, vol. 7, pp. 96–105.

Karring et al., "New Attachment Formation on Citric Acid and Non–Citric Acid Treated Roots," Journal of Periodontal Research, 1984, vol. 19, pp. 666–669.

Karring et al., "New Attachment Formation on Teeth with a Reduced but Healthy Periodontal Ligament," Journal of Clinical Periodontology, 1985, vol. 12, pp. 51–60.

Karring et al., "Potentials for Root Resorption During Periodontal Wound Healing," Journal of Clinical Periodontology, 1984, vol. 11, pp. 41–52.

Lindhe et al., "Connective Tissue Reattachment as Related to Presence or Absence of Alveolar Bone," Journal of Clinical Periodontology, 1984, vol. 11, pp. 33–40.

Line et al., "Relationship Between Periodontal Injury, Selective Cell Repopulation and Ankylosis," J. Periodontol., Oct., 1974, vol. 45, No. 10, pp. 725–730.

Linghorne, "The Sequence of Events in Osteogenesis as Studied in Polyethylene Tubes," Annals of New York Academy of Sciences, 1960, vol. 85, pp. 445–460.

Magnusson et al., "Connective Tissue Attachment Formation Following Exclusion of Gingival Connective Tissue and Epithelium During Healing," Journal of Periodontal Research, 1985, vol. 20, pp. 201–208.

Melcher, "On the Repair Potential of Periodontal Tissues," J. Periodontology, May 1976, vol. 47, No. 5, pp. 256–260.

Melcher, "Repair of Wounds In The Periodontium of the Rat. Influence of Periodontal Ligament on Osteogenesis," Archs. oral Biol., 1970, vol. 15, pp. 1183–1204.

Melcher and Dreyer, "Protection of the Blood Clot in Healing Circumscribed Bone Defects," The Journal of Bone and Joint Surgery, May 1962, vol. 44B, No. 2, pp. 424–430.

Murray et al., "Experimental and Clinical Study of New Growth of Bone in a Cavity," American Journal of Surgery, Mar. 1957, vol. 93, pp. 385–387.

Nyman, "Parodontal Regeneration—Utopi Eller Realitet," Ontolologi '90, 1990 (German article).

Nyman, "The Regenerative Potentials of the Periodontium—Theory and Practice of the New Attachment Procedure," Vortrag Bayerischer Zahnarztetag 1984 (German article).

Nyman and Karring, "Regeneration of Surgically Removed Buccal Alveolar Bone in Dogs," J. Periodontal Res., 1979, vol. 14, 86–92.

Nyman et al., "Bone Regeneration Adjacent to Titanium Dental Implants Using Guided Tissue Regeneration: A Report of Two Cases," The International Journal of Oral & Maxillofacial Implants, 1990, vol. 5, No. 1, pp. 9–14.

Nyman et al., "Bone Regeneration in Alveolar Bone Dehiscences Produced by Jiggling Forces," Journal of Periodontal Research, 1982, vol. 17, pp. 316–322.

Nyman et al., "Healing Following Implantation of Periodontitis–affected Roots in Gingival Connective Tissue," Journal of Clinical Periodontology, 1980, vol. 7, pp. 394–401.

Nyman et al., "Healing Following Reimplantation of Teeth Subjected to Root Planing and Citric Acid Treatment," Journal of Clinical Periodontology, 1985, vol. 12, pp. 294–305.

Nyman et al., "New Attachment Following Surgical Treatment of Human Periodontal Disease," Journal of Periodontal Research, 1982, vol. 9, pp. 290–296.

Nyman et al., "New Attachment Formation By Guided Tissue Regeneration," Journal of Periodontal Research, 1987, vol. 22, pp. 252–254.

Nyman et al., "Role of 'Diseased' Root Cementum in Healing Following Treatment of Periodontol Disease," Journal of Periodontal Research, 1986, vol. 21, pp. 496–503.

Nyman et al., "Role of 'Diseased' Root Cementum in Healing Following Treatment of Periodontal Disease," J. Clin. Periodontol., 1988, vol. 15, pp. 464–468.

Nyman et al., "The Regenerative Potential of the Periodontal Ligament: An Experimental Study in the Monkey," Journal of Clinical Periodontology, 1982, vol. 9, pp. 257–265.

Pontoriero et al., "Guided Tissue Regeneration in Degree II Furcation–Involved Mandibular Molars," J. Clin. Periodontol., 1988, vol. 15, pp. 247–254.

Pontoriero et al., "Guided Tissue Regeneration in the Treatment of Furcation Defects in Mandibular Molars," J. Clin. Periodontol., 1989, vol. 16, pp. 170–174.

Pontoriero et al., "Guided Tissue Regeneration in the Treatment of Furcation Defects in Man," J. Clin. Periodontol., 1987, vol. 14, pp. 618–620.

Prichard, "Criteria for Verifying Topographical Changes in Alveolar Process After Surgical Intervention," Journal of American Society of Periodontists, Mar./Apr. 1966, vol. 4, No. 2, pp. 71–76.

Prichard, "The Diagnosis and Management of Vertical Bony Defects," J. Periodontol., Jan. 1983, vol. 54, No. 1, pp. 29–35.

Prichard, "The Roentgenographic Depiction of Periodontal Disease," JOSPD, Mar./Apr. 1973, vol. 3, No. 2.

Radell and Cassingham, "A Clinical Evaluation of Proplast as a Periodontal Implant Material," J. Periodontol., Feb. 1980, vol. 51, No. 2, pp. 110–115.

Schroeder and Lindhe, "Conversion of Stable Established Gingivitis in the Dog into Destructive Periodontitis," Archs oral Biol., 1975, vol. 20, pp. 775–782.

Seibert and Nyman, "Localized Ridge Augmentation in Dogs: A Pilot Study Using Membranes and Hydroxyapatite," J. Periodontol., Mar. 1990, vol. 61, pp. 157–165.

Shiloah, "The Clinical Effects of Citric Acid and Laterally Positioned Pedicle Grafts in the Treatment of Denuded Root Surfaces," J. Periodontol., Nov. 1980, vol. 51, No. 11, pp. 652–654.

Thilander et al., "Bone Regeneration in Alveolar Bone Dehiscences Related to Orthodontic Tooth Movements," European Journal of Orthodontics, 1983, vol. 5, pp. 105–114.

SURGICAL ELEMENT AND METHOD FOR SELECTIVE TISSUE REGENERATION

This application is a continuation of application Ser. No. 926,604, filed on Aug. 5, 1992, now abandoned which in turn was a continuation-in-part of application Ser. No. 07/689,236, filed on Jun. 18, 1991, now abandoned. Priority of application Ser. No. 88/04641, filed on Dec. 23, 1988, in Sweden, and application PCT/SE 89/00746, filed on Dec. 22, 1989, is claimed under 35 U.S.C. § 119.

FIELD OF THE INVENTION

The present invention relates to element and method for selective regeneration of any tissues in a living human or animal body tissues subjected to healing and where these tissues, preferably, should or unconditionally must be favored or unfavored in relation to each other with regard to time and/or location and space during healing of wounds in which specifically ordered tissue formation is aimed at. The element and method of the present invention are applicable within several areas throughout the whole body in situations where selected regeneration of the different tissues participating in the wound healing process is desired.

More particularly, the present invention relates to an element for guided or controlled tissue regeneration to be utilized for selected influence on the healing process during regeneration of supporting tissues adjacent to teeth and dental implants, as well as, during healing after periapical surgery. However, generally the element can be used also in connection with bone surgery to control bone fill of bone cavities resulting from cysts and malformations and of diastases following bone fractures.

BACKGROUND OF THE INVENTION

Although the subject of surgical techniques aimed at excluding certain tissues from a wound area was appreciated in the late fifties and early sixties, the biological concept of guided or selective tissue regeneration was not systematically investigated and scientifically proven until the late seventies and early eighties. The concept was applied on regeneration of lost periodontal tissue and presented the first evidences on the validity of the concept. The concept means that it is possible to influence the healing process by guiding the different tissues participating in that process. The guidance can be achieved by the aid of physical elements implanted between the tissues to be influenced. Thus, if it is desired that a certain space should be filled by a certain type of tissue, the cells of this tissue should favorably be allowed to enter the space at the same time that the migration of the cells of other tissues into said space is hindered. The validity of this biological concept has been documented in several scientific papers by different authors.

It has not been possible previously to regenerate lost tooth supporting tissues to a clinically relevant degree. However, studies have shown that periodontal attachment and support structures may be regenerated. Given the proper conditions, cells of the periodontal ligament can be stimulated to repopulate a previously diseased tooth root surface. This concept offers the hope for renewing periodontal structures once thought to be lost permanently due to disease. Studies suggest that, after periodontal surgery, a race begins among the cells from the four types of periodontal tissues, gingival epithelium, gingival connective tissue, alveolar bone and periodontal ligament, to repopulate the previously diseased root surface. If uncontrolled, the healing process usually results in downgrowth of cells from the gingival epithelium along the surface of the gingival connective tissue immediately lateral to the root surface, thereby preventing migration of cementoblasts from the adjacent periodontal ligament to form new cementum on the denuded root surface to which new periodontal fibers can attach. Even if the gingival connective tissue, also quick to take part in the healing process, occupies the space immediately lateral to the root surface, thereby hindering the downgrowth of epithelial cells, there will be no true new attachment between that type of tissue and the root surface but rather a substantial risk of root resorption.

If the alveolar bone, which usually regenerates more slowly than the gingival epithelium and connective tissue, happens to fill up parts of the space adjacent to the root surface and thereby reaches the root surface, the bone will form an ancylotic union with the part of the root which is unprotected by root cementum and periodontal ligament tissue.

If, on the other hand, cement-producing cells, i.e., cementoblasts from the remaining adjacent and intact periodontal ligament tissue, reach the denuded root surface area, they will produce cementum with inserting connective tissue fibers on the dentine surface, i.e., a true, new periodontal ligament is formed uniting the root with the surrounding bone and gingival connective tissue. Unfortunately, the cementoblasts do not normally reach more than a negligible part of the previously diseased root surface immediately adjacent to the intact periodontal ligament due to the fact that cells of the other tissues occupy the wound area. However, research into guided tissue regeneration has shown that the cementum and periodontal ligament producing cells have the ability to become established on the root surface if that surface is isolated from other tissues during healing. This isolation during the initial healing process enables the different periodontal structures to become re-established in a proper sequence resulting in a new periodontal attachment.

An element for regeneration of periodontal tissues should be constructed so that:

1) the gingival connective tissue is stimulated to rapidly grow into the element without passing too quickly through the element in order to:
   a) block the downgrowth of the gingival epithelium along the gingival side of the element;
   b) attach the gingival flap to the element, thereby avoiding flap (gingival) recession with denudation of the periodontal wound area;
2) ingrowth of soft tissue between the element and the periodontal tissue surrounding the root surface is prevented;
3) the element is tightly attached to the cervical area of the root preventing downgrowth of soft tissue and microorganisms between the root surface and the element;
4) the element occupies as little cervical space as possible adjacent to the root surface to permit periodontal ligament cells to regenerate as coronal as possible;
5) the element can be placed either alongside the root surface leaving satisfactory space for periodontal ligament regeneration and/or in a suprabony provision to permit periodontal ligament regeneration and alveolar bone regeneration on the tooth side of the element; and
6) the element, preferably, is biodegradable in such a way that eventually it will disappear during the healing process without adverse effect to the organism.

In addition to the periodontal application, any bone or bone area throughout the whole body available for surgical intervention can be treated by using the method and element of the present invention. The aim of the treatment might be a predictable filling out of bone defects of different sizes and shapes in the edentulous jaw bone or adjacent to teeth or bone-anchored implants, as well as, bone defects anywhere else within the body as in the maxillofacial bones, in the skull bones, in the long bones, in the hand and foot bones, and in the back bones. The defects might have well-defined borderlines or successively pass into the surrounding bones and their bottom and wall surfaces can contain more or less of compact (cortical) bone. The defects might be so narrow so they rather would be defined as bone depressions than bone defects. In fact, there are many sites where the bone surface to be chosen for regeneration is flat or convex rather than concave, but where there are strong indications for building up rather than filling out bone. The bone defect can also include a fracture with more or less advanced discontinuity. Furthermore, the defect can be of the through-type, as is the case with some skull bone and jaw bone defects. The present invention may also be used in situations where there are indications for elongation (or shortening) of bones, for instance, of jaw bones and long bones. The technique can be used to collect bone for transplantation.

There are many causes of the above-described bone defects, such as congenital defects, traumatic lesions, defects caused by tooth extractions, osteitis, cysts, tumors, periodontal destructions, bone resorptions due to overloading, infections or internal diseases. These defects may be functional and/or aesthetic in nature. Other therapeutic measures might be based solely on aesthetic indications for correction of deformities or aesthetic "improvements" of the appearance. Many of the mentioned indications will be elucidated and described in detail below in conjunction with the different embodiments and exemplifications.

There are still other areas of indication within the human or animal body for the technique of the present invention, such as selective regeneration of more or less specialized tissues, for example, membranes demarcating body cavities and/or separating different tissues and organs from each other, as well as, for selective regeneration of different tissues within the organs, of the organs themselves in relation to the surrounding tissues, or of nerves. Examples of membranes are the periosteum, the membrane of the brain, and the peritoneal membrane; while examples of organs are the liver, the throat, the ventricle, the kidney, the heart, and the pancreas. Also, muscle tissue and tendons should be possible to regenerate with the element of the present invention.

So far, treatments of bone defects based on most of the above-mentioned indications have either not been performed or have comprised grafting with either natural or synthetic materials to fill out the defect or increase the tissue volume. The natural grafting materials can be harvested from iliac, rib, oral or other bone of the individual himself (autotransplantation) or from another individual (allotransplantation). Synthetic materials include particles or blocks, for instance, of either solid or porous tricalciumphosphates (TCP), hydroxylapatites (HA), or synthetic polymers. The use of natural grafting materials demands surgical intervention in at least two sites and the extra surgical procedures are often painful. In addition, there is a low predictability for proper bone regeneration with both natural and synthetic graft materials since the possible ingrowth of bone cells very often is jeopardized by the faster growing fibrous tissue cells (fibroblasts) which produce soft connective tissue instead of bone tissue. Furthermore, the synthetic materials have a tendency to migrate away from the area, thereby minimizing the intended increase in bone volume.

Application of the concept of guided tissue regeneration, preferably, on reformation or new formation of bone tissue, briefly means that the space to be filled with the bone tissue must be available for the bone-forming cells at the same time that it must be separated from the non-desired tissues, for instance, soft tissues such as connective tissue and epithelium. It should be clearly understood that the bone-forming cells (osteoblasts) are residing mainly along the endosteal surfaces of the spongious (cancellous) bone. It is, therefore, important to assure the best possible communication between the endosteal surfaces and the space to be filled with bone. This means that compact bone, which covers the spongious bone and blocks the communication should, at least in part, be removed to optimize the ingrowth of these cells into the space. It is advisable to first remove all soft tissue within the space in question. Perforations in the form of round holes or slots should be made through the remaining compact bone to insure that there is as much direct connection as possible between the space and the spongious bone.

The soft tissues must be kept out of the space by a convenient means from the very beginning of the wound healing process. This means should reliably preclude ingrowth of soft tissue cells through itself or via any lateral space between the element and the surrounding bone. If the space is more or less occupied by soft tissue, a complete occupation of the space by bone tissue will be prevented.

An element to be successfully used for guided bone tissue regeneration should therefore:

1) be constructed to insure that soft tissue cells cannot pass the element or that ingrowth of soft tissue cells into the element is delayed to such an extent that the bone tissue regeneration in the desired space is not jeopardized;

2) be constructed to prevent the ingrowth of soft tissue between the element and the bone surrounding the space or between the element and an endossias implant;

3) be able to maintain the space to be filled;

4) permit transport of bone cells via the perforations lateral to the bone space into the space to be filled;

5) be constructed to provide the best possible stability of the tissue, as well as, the element;

6) minimize the risk of rupture of the soft tissue flap covering the wound area; and 7) preferably be biodegradable in such a way that eventually it will disappear during the healing process without adverse effect on the organism.

U.S. Pat. No. 5,032,445 discloses the use of a biocompatible porous material, such as expanded polytetrafluoroethylene (PTFE), for separating the gingival tissue from the tooth surface in an area where periodontal disease is present, or for treatment of bony defects. This material is marketed under the registered trademark GORE-TEX, which is owned by W. L Gore and Associates. This material comprises an irregular network of fine fibrils, which forms a porous microstructure including open porosities. The material is intended to separate the gingival epithelium and connective tissue from the periodontal ligament and the alveolar bone during the healing process. When used for regeneration of periodontal tissues, the most coronal portion of the material includes a collar with slightly coarser fibrils of PTFE. This collar allows for ingrowth of connective tissue thereinto. This ingrowth of tissue will prevent epithelial downgrowth along the surface of the material facing the connective tissue. Thus, the material creates a protected area adjacent to the periodontal wound so that cells from the remaining periodontal ligament can repopulate the root surface for periodontal regeneration in competition with the cells of the alveolar bone.

However, the material must be properly positioned to successfully prevent the downgrowth of gingival epithelial tissue. In the GORE-TEX material, the anchoring ligature of the material is located directly below the coronal portion thereof, which often prevents positioning the entire material a sufficient distance below the gingival margin. If the coronal portion of the PTFE material is placed close to the gingival margin, the epithelial downgrowth will pass the limited coronal portion of the material and continue in the apical direction without hindrance because ingrowth of connective tissue does not predictably occur into the very small pores of that part of the material. The result will be a pocket formation between the gingiva and the material followed by gingival recession and exposure of the material. This, in turn, will jeopardize the protection of the wound environment which is an important condition for periodontal regeneration. In addition, the epithelial downgrowth will result in the formation of a pocket with accumulation of micro-organisms causing infection, thereby jeopardizing the periodontal regeneration.

Furthermore, the GORE-TEX material functions only in part selectively because it does not control the relationship between the healing sequences of the bone and periodontal ligament tissues. During the healing process, if the bone tissue regenerates along the root surface before the periodontal ligament tissue is allowed to attach to the root surface, an ankylosis formation will occur.

In addition, the GORE-TEX material often collapses into periodontal defects, thus, jeopardizing the objective of creating a space between the tooth and the material.

The biostable non-degradable materials tested so far for periodontal use, including the GORE-TEX material, must be removed after their function has been fulfilled, i.e., when the periodontal ligament cells have repopulated the denuded root surfaces. This means that a second operation must be performed after an initial healing period. The removal operation is done typically in 1 to 3 months after the first operation. This involves significant costs, additional risks (such as the possibility of postoperative infection), and troubles for the patient.

When used for treating bone defects in general, the GORE-TEX material is characterized by having a central portion, the porosity of which is such that growth of soft tissue through said portion is prevented. The peripheral portion of the material, intended to be fixed in laminar relationship to the bone surface surrounding the bone defect to be regenerated, is characterized by having porosities which support connective tissue ingrowth. The laminar relationship between the material and the surrounding bone surface means that the bone surface, which preferably should be perforated, cannot be utilized for delivering bone cells into the bone defect, such delivery often being of importance for the regeneration.

In addition, the GORE-TEX material often tends to collapse into the bone defect.

An ideal material for guided tissue regeneration should be biodegradable because such a material is degraded in a biological environment and, accordingly, no removal operation is necessary. However, attempts to utilize biodegradable materials have failed due to disturbances of the healing process. For instance, well-known, natural, non-biostable materials like collagen and catgut, which are at least partially biodegradable, are not suitable for guided tissue regeneration because they may rapidly induce (in 1 to 2 weeks) inflammatory reactions in living tissues (see, e.g., E. Echeverria and J. Jimenez, Surgery, 131 (1970) 1–14 and J. B. Herrmann, R. J. Xelly and G. A. Higgins, Arch. Surg., 100 (1970) 486490). The degradation of these materials is dependent upon the action of proteolytic enzymes (R. W. Postlethwait in "Davis-Christopher Textbook of Surgery" (D. C. Sabiston, Jr., ed.), 10th ed., Vol. I, Saunders Co., Philadelphia-London-Toronto, 1972, 307–318) which typically leads to early tissue reactions, which interfere with the regeneration process and, therefore, can seriously jeopardize the predictability of regeneration. The biodegradable and non-biodegradable materials utilized so far for periodontal purposes have neither been able to predictably differ regeneration of periodontal ligament tissue from regeneration of surrounding alveolar bone tissue nor have they been fully reliable as far as their space-making properties are concerned. Furthermore, the collagen materials, as well as other synthetic materials, have not been given a design that fulfills the requirements set forth above.

SUMMARY OF THE INVENTION

An object of the present invention is to provide an element which can be placed within a desired area of the body in such a way that a predictable healing sequence is achieved by the element predictably creating space for regeneration of tissue.

This object may be achieved by providing an element for controlled tissue regeneration, comprising at least one malleable member forming opposite sides, and at least one spacer means for separating said member on at least one side thereof from an adjacent surface.

In addition, in the case of using a biodegradable material, there is need for only one surgical procedure which is advantageous both with respect to costs and the patient's comfort.

The element should, preferably, include a totally biodegradable material but could also include a partly biodegradable or a non-biodegradable material. It has been found that the material of the element should not be too reactive in its resorption behavior and should retain its mechanical strength, at least partially and at least during the first four weeks in vivo after implantation. In addition, the material should induce only mild tissue reactions. Thus, the degradation of the element, preferably, should not start earlier than 4 to 6 weeks after the surgical implantation resulting in an initial period of healing free from disturbances. Also, after the beginning of the degradation of the element, the tissue effects should be minimal.

Suitable biodegradable materials include polymers such as polyglycolide (PGA), polylactide (PLA), stereocopolymers of PLA, copolymers of PLA, and degradable ceramic materials. Other examples are hyaluronic acids and mixtures of the mentioned materials.

Still, other examples are polydesoxazon, polyhydroxy butyric acid, copolymers of polyhydroxy butyric acid and hydroxy valeric acid, and polyesters of succinic acid.

Suitable non-biodegradable materials could be, but are not limited to, polyurethanes, polyesters, expanded polytetrafluorethylene and combinations of these materials.

The elements should be very thin and, preferably, the maximum thickness of a single sheet element or each sheet of a multiple sheet element or material should be 200–300 µm.

The separating means of the element, such means separating the element from adjacent tissue such as bone tissue, a root surface, or soft tissue or separating adjacent sheets forming parts of a multiple sheet element, preferably, are formed as protrusions integral with the element, or comprise separate members. The separating means (spacers) are, preferably, dimensioned to keep a distance of 100–500 μm between adjacent sheets. These spacers, however, also can be so long that they are able to prevent an element covering a bone defect from collapsing thereinto.

The separating means also can include a gel having macromolecular structure applied between the element and the adjacent surface from which the element should be spaced.

The present invention also provides a method for selected influence on the healing process in connection with tissue regeneration, wherein a defined space for tissue growth is provided between an implanted element and adjacent tissue. The space can be maintained by means of spacers on the element, but the element itself may also have sufficient inherent shape stability so as to maintain the space without spacers being provided.

The element, preferably, should be perforated to allow for transport of body fluids to and from the surrounding tissues for nutrition. In addition, such perforation secures ingrowth of the local soft tissue to stabilize the element and provide for integration of soft tissue, thereby avoiding tissue retraction and denudation of the wound area.

In periodontal use, there should be secured in the cervical (tooth-neck) region a tight anchorage (retention) of the element against the root surface. This can be achieved by a perforation pattern in the cervical region of the element comprising holes and tracks which can harbor suitable material for gluing the element to the crown or root surface by the aid of, for instance, resin.

In the preferred embodiment for the periodontal use, the element forms a through passage in the cervical region to receive therein a ligature for anchoring the element to the tooth. The ligature can be displaceable longitudinally or be non-displaceable in the passage. The element, preferably, has a rib integral therewith, which extends along the passage to be applied against the tooth. The cervical portion of the material facing the gingival tissue is, preferably, characterized by preformed cavities which allow for ingrowth of connective tissue. The cavities could be designed as described in the Swedish Patent No. 8405568-0. Such undercut cavities could advantageously also be included in the gingival portion of the whole element. The ingrowth of connective tissue into the cavities, as well as the tight connection of the element to the tooth, arrests epithelial cell migration apically along the element.

Therefore, in broad summary, the invention comprises an article adapted for controlled tissue regeneration having a first member having opposite sides, and further having at least one spacer means for separating the member on at least one side thereof from an adjacent surface. The article may further include a second member that may be disposed parallel to the first member, and an additional spacer means that separates the first member from the second member, where the at least one spacer means is adapted to enable the regeneration of periodontal ligament tissue.

A more specific article comprises an additional spacer means, wherein the at least one spacer means is adapted to separate the first member from an adjacent surface of a root of a tooth, and wherein the additional spacer means is disposed on the opposite side of the first member and is adapted to separate that member from a different surface. Such an article may also have a second member having a surface opposite the first member, wherein the additional spacer means is adapted to separate the first member from the second member.

The invention also includes a method for creating a space for controlled regeneration of tissue. The method comprises disposing at the site where the tissue is to be regenerated, an article comprising an element as described above, and having at least one spacing means adapted to maintain a space between the element and an adjacent surface of a tooth, a bone, or an implant.

DETAILED DESCRIPTION OF THE DRAWINGS

Figure 1:
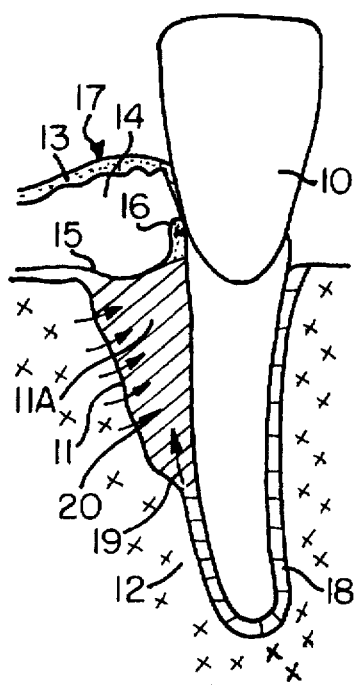
FIG. 1 is a buccal side view of a prior art element (seen from the lip).
Figure 2:
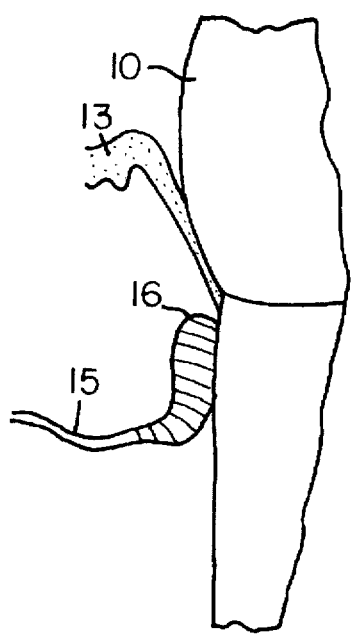
FIG. 2 is an enlarged fragmentary side view and cross-sectional view showing the connection of the element of FIG. 1 to the root of the tooth.
Figure 3:
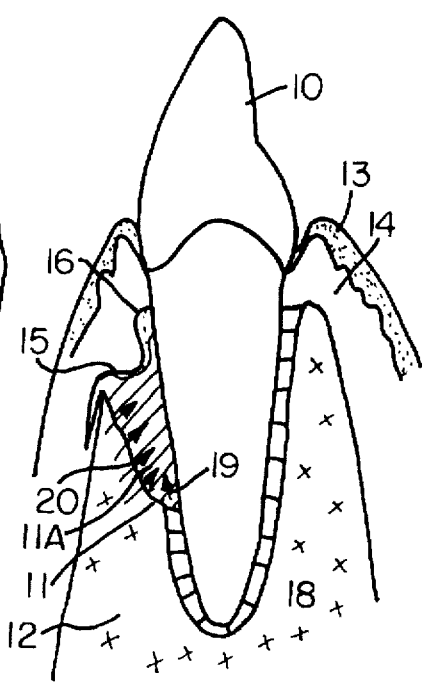
FIG. 3 is a proximal (lateral) view of the tooth in FIGS. 1 and 2, with the adjacent tissues being shown in vertical cross-sectional view.

Referring to FIGS. 1 to 3 of the drawings, there is shown a one-rooted tooth 10 with a bone defect 11 in the bone tissue 12, extending over two of the root surfaces. Soft tissues, epithelium 13 and connective tissue 14, cover the bone tissue. The bone defect 11 has been debrided and is filled with a blood clot 11A. A prior art material 15 has been placed in its position with a cervical portion 16 sutured around the neck of the tooth. The previously reflected soft (mucoperiosteal) flap 17 has been repositioned and covers the material. It is expected that the tissues which have been given preference, i.e., the periodontal ligament tissue 18 and the bone tissue 12, regenerate without being hindered by downgrowing epithelium 13 and connective tissue 14, as indicated by a large arrow 19 and small arrows 20, respectively. There is, however, a risk that bone tissue regeneration will be faster than periodontal ligament tissue regeneration, thus preventing a regeneration of true periodontal ligament tissue along the root surface, and instead causing so-called ankylosis, i.e., bone tissue in direct contact with the root surface without intervening soft tissue. Such an arrangement has a considerable potential to cause more or less extensive resorptions of the root dentine, ultimately destroying the whole root. This risk probably increases the narrower the bone defect, i.e., the shorter the distance between the bone wall and the root surface, but there are probably other, so far unknown factors that govern the relative regeneration velocity of these two types of tissue.

Figure 4:
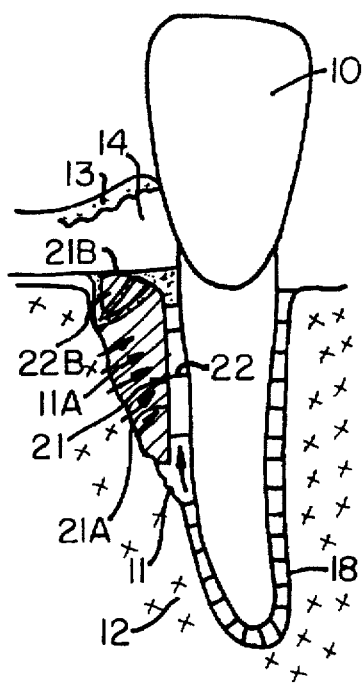
FIGS. 4 to 6 are views similar to FIGS. 1 to 3 illustrating a first embodiment of the present invention.
Figure 5:
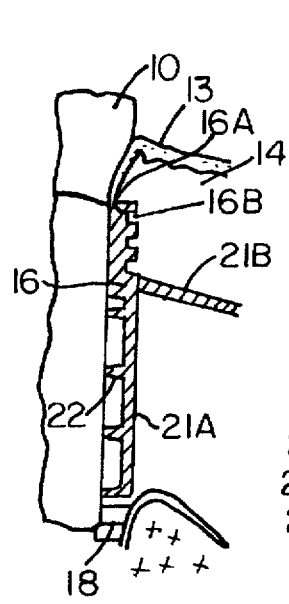
Figure 6:
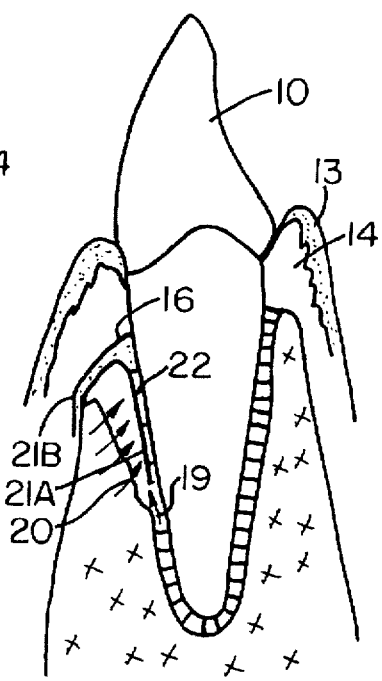

In order to fully eliminate the risk of "bone-to-root-healing," the present invention permits full control over the healing sequences of tissues. Referring to FIGS. 4 to 6, an embodiment of the present invention will be discussed. These figures illustrate the same tissue destruction as in FIGS. 1 to 3, but there is a decisive alteration in the design of the element generally designated 21, which has a first portion 21A close to the root surface but kept at a distance therefrom which can range from 10 µm to 1000 µm, preferably from 100 µm to 500 µm, by means of protrusions, bosses, or similar means 22 forming spaces into which the periodontal ligament tissue 18 should regenerate, and a second portion 21B extending transversely from the root at the upper end of portion 21A, preventing the gingival tissue from growing into the defect. Also, this portion, preferably, provides spacers 22B reaching from the element portion 21B to the bone wall in order to eliminate the risk of element collapse in case of wide defects as the element itself must be rather soft to be adequately shaped. Accordingly, the spacers should be relatively long and stiff when used to support elements protecting wide defects or forming other tent-like housings, and the necessary stiffness can be imparted to them by reinforcing the spacers or by forming the spacers of material other than that which the element is made of, or by including into the spacers the same mixture of materials as in the element itself, but in another ratio. Thus, the spacers can include a combination of materials of a biodegradable and/or biostable type.

A cervical collar 16 is glued to the tooth root and/or is sutured to the root as shown at 16A. The collar portion is formed with undercut cavities 16B, preferably, designed as described in the Swedish Patent No. 8405568-0, as bottom holes or grooves.

The element is advantageously perforated or at least partially perforated or microporous.

The element can be manufactured, preferably, by molding, but can also consist of fibers by knitting, weaving or by non-woven techniques. Such materials or devices can contain biodegradable polymeric material as fiber binding material, or the fibers can be bound to each other by only means of physical forces.

Also, biodegradable ceramic fibers, including calcium-phosphate or hydroxyapatite fibers, can be used.

To help the spacers in preventing collapse of the element when protecting wide defects, the element could also be provided with local fiber reinforcements in the form of stroma not jeopardizing the malleability of the element.

Clinical observations have indicated that with an element including the biodegradable materials mentioned above, sufficient healing of periodontal tissue may occur between four to six weeks. Up to four weeks, the materials cause only slight cellular response and, therefore, behave during these four first weeks much in the same manner as biostable inert elements (such as polytetrafluoroethylene). After four weeks, the healing of periodontal tissues has proceeded significantly and the resorption of the element can accelerate without significantly disturbing the regenerated periodontal tissues. Because the material, when biodegradable, disintegrates and disappears by hydrolysis, no removal operation is later necessary.

The space between the portion 21A associated with the root surface, and the bone wall, i.e., the bone defect 11, can also be more or less occupied by a three-dimensional mesh. The mesh, consisting of biodegradable threads of one of the materials for the element mentioned above, should make the regeneration of bone easier.

The material of the element also can contain different additives because of different purposes to facilitate the processing, to modify the properties, to help the surgical installation, or to give to the material and/or element totally new biofunctional properties. Such additives are, e.g., colors, plasticizers, antioxydants, and biofunctional additives such as drugs (e.g., antibiotics) and growth hormones. Thus, the body of the element can be loaded with slowly released bone growth stimulating components, as can also the parts of the element facing the bone defect. The spacers and the side of the element portion 21 facing the root surface, preferably, are loaded with slowly releasing components stimulating the regeneration of periodontal ligament tissue. The surface facing the gingival tissue, in particular the collar portion, can be loaded with slowly released components stimulating the ingrowth of gingival tissue into the material. The threads, and the element itself, in the case of being loaded with such components, are constructed to either physically (microcavities) and/or chemically bind the different components. Suitable components to be used for loading are protein components to stimulate bone regeneration, enamel matrix components, e.g., from pigs or bovine to stimulate periodontal tissue regeneration, and growth hormones such as TGF-alfa, TGF-beta, EGF, PDGF, FGF and IGF-1.

The element, thus, permits not only a discrimination of the different tissues but also a predictable determination of the amount of regenerated tissue due to the size of the spacers and an individual shaping of the marginal portion of the element. In addition, the size of the perforations of the element can be varied as is necessary in order to govern the transportation of tissue fluid components, as well as, the transmigration of the tissue cells responsible for the rebuilding of the different types of tissue.

Figure 7:
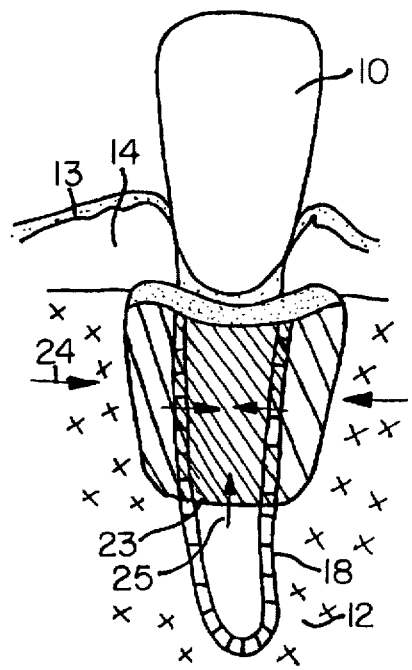
FIGS. 7 to 9 are views similar to FIGS. 1 to 3 illustrating a second embodiment of the present invention.
Figure 8:
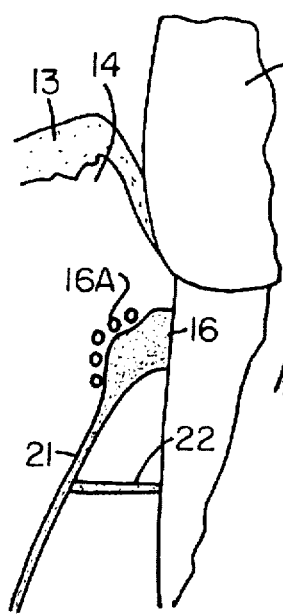
Figure 9:
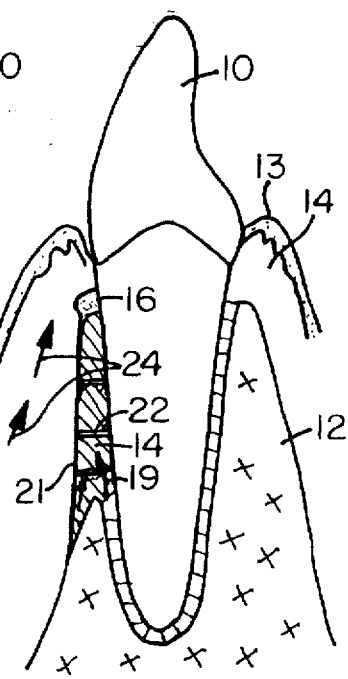

FIGS. 7 to 9 show a one-rooted tooth from the same aspects as in FIGS. 4 to 6 but with a denuded buccal root surface indicated at 23 in FIG. 7 by shading. The element 21 is placed to cover the denuded root surface which has been thoroughly cleaned. A mucoperiosteal flap then has been raised to uncover it and the surrounding alveolar bone 12. The element also covers the bone adjacent to the denuded root surface. The cervical portion 16 of the element is glued or otherwise attached to the root surface and extra-long spacers 22 define the space between element 21 and the root surface. This space is occupied by a blood clot 14 after which the mucoperiosteal flap is mobilized in a coronal or lateral direction (towards the crown of the tooth or from either side of the root, respectively, as indicated by large arrows 24) and sutured tight to the tooth in its new position at 16A. It is expected that the favourized tissues, i.e., periodontal ligament and bone tissue (small arrows), to a considerable degree will regenerate in coronal direction and from the lateral regions as indicated by small arrows 25, to cover the denuded root surface. The element, however, does not discriminate between periodontal ligament tissue and bone tissue, thus, creating a risk of ankylosis due to faster bone regeneration than periodontal ligament regeneration. The element in FIGS. 10 to 12 eliminates such a risk.

Figure 10:
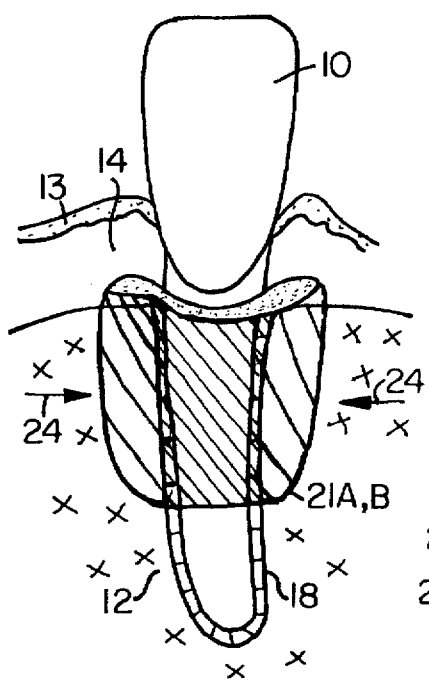
FIGS. 10 to 12 are views similar to FIGS. 1 to 3 illustrating a third embodiment of the present invention.
Figure 11:
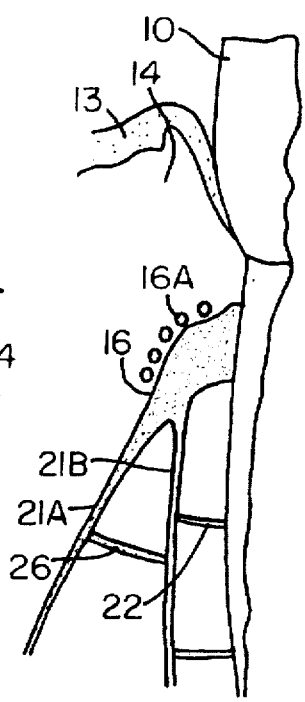
Figure 12:
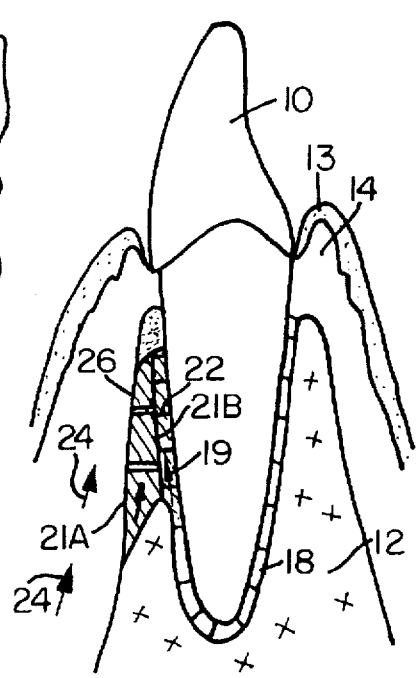

FIGS. 10 to 12 illustrate the same anatomical situation as in FIGS. 7 to 9 but with an element which discriminates between the bone regeneration and the periodontal ligament regeneration as illustrated in the proximal view of FIG. 12. Extra spacers 26 are provided between an outer element portion 21A and an inner element portion 21B to maintain the space for bone regeneration. As previously discussed, this space can, preferably, be supplied with substances to stimulate the bone regeneration.

Figure 13:
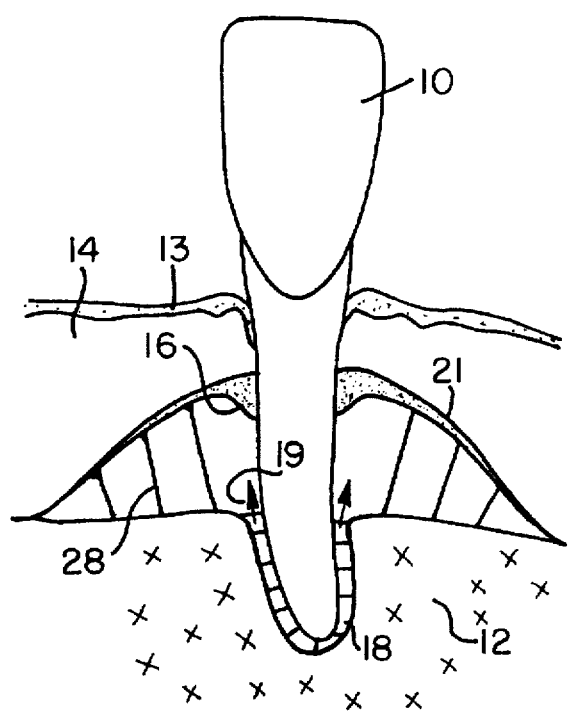
FIGS. 13 and 14 are views similar to FIGS. 1 and 3 illustrating a fourth embodiment of the present invention.
Figure 14:
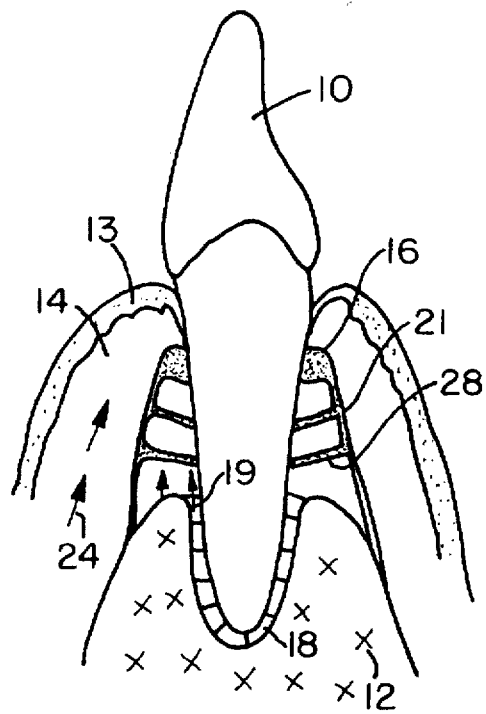

FIGS. 13 and 14 show the same aspects as in FIGS. 1 to 12 but with so-called horizontal bone destruction, i.e., the destruction of bone is equal all around the root with no bone defects surrounded by bone walls. The element is basically constructed as illustrated in FIGS. 7 to 9 and comprises a single element layer 21 but with specially-designed spacers 28 reaching from the element to the root surface or the bone. These spacers at the same time can serve as guiding structures for regeneration of the bone tissue in coronal direction (in direction of the tooth crown). The stiffness of this type of element is adjusted to withstand the pressure from the soft tissues. This is done during the production procedure by mixing the element material components in certain ratios or by reinforcing the spacers and the element by other materials. Also, this type of element cannot, however, predictably discriminate between the bone and the periodontal tissue regeneration. A discriminating element suitable for this type of bone destruction is shown in FIGS. 15 and 16.

Figure 15:
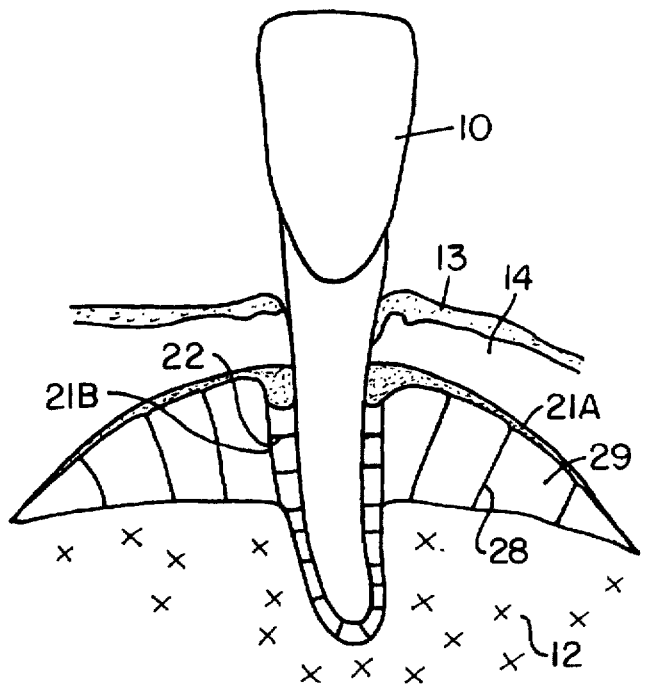
FIGS. 15 and 16 are views similar to FIGS. 1 and 3 illustrating a fifth embodiment of the present invention.
Figure 16:
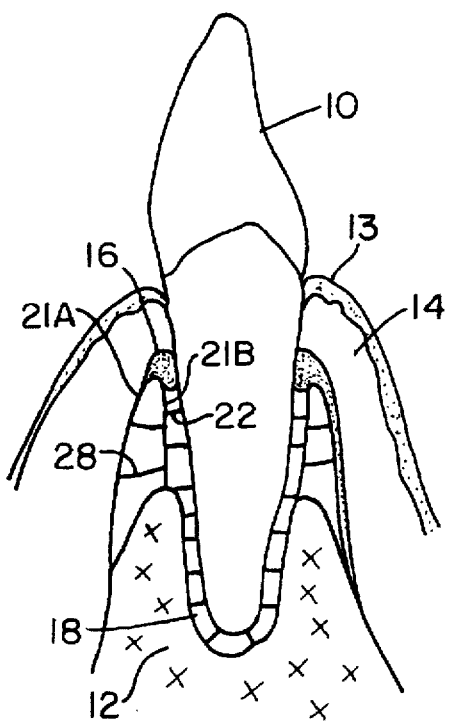

FIGS. 15 and 16 show the same bone destruction situation as in FIGS. 13 and 14. However, the element again has two portions, an outer portion 21A, intended to separate the connective tissue 14 from a space 29 into which the bone tissue 12 should regenerate, and an inner portion 21B separating this space from the space adjacent to the root surface into which the periodontal ligament tissue 18 should regenerate. The element portions 21A and 21B are held in the proper positions by spacers 28 and 22, respectively. Thus, the risk of causing ankylosis, i.e., bone regeneration in close contact with the root surface, is eliminated.

Figure 17:
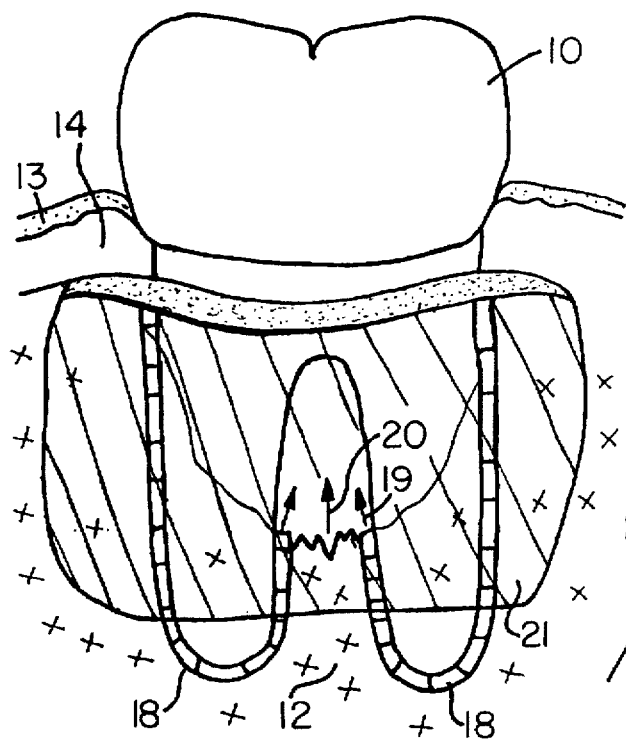
FIGS. 17 and 18 are views similar to FIGS. 1 and 3 illustrating the second embodiment of the present invention as in FIGS. 7–9, applied, however, to a two-rooted tooth.
Figure 18:
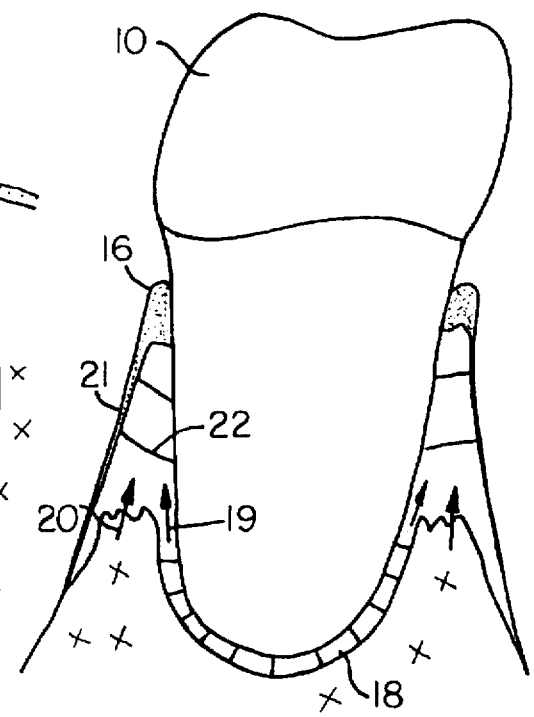
Figures 19, 20:
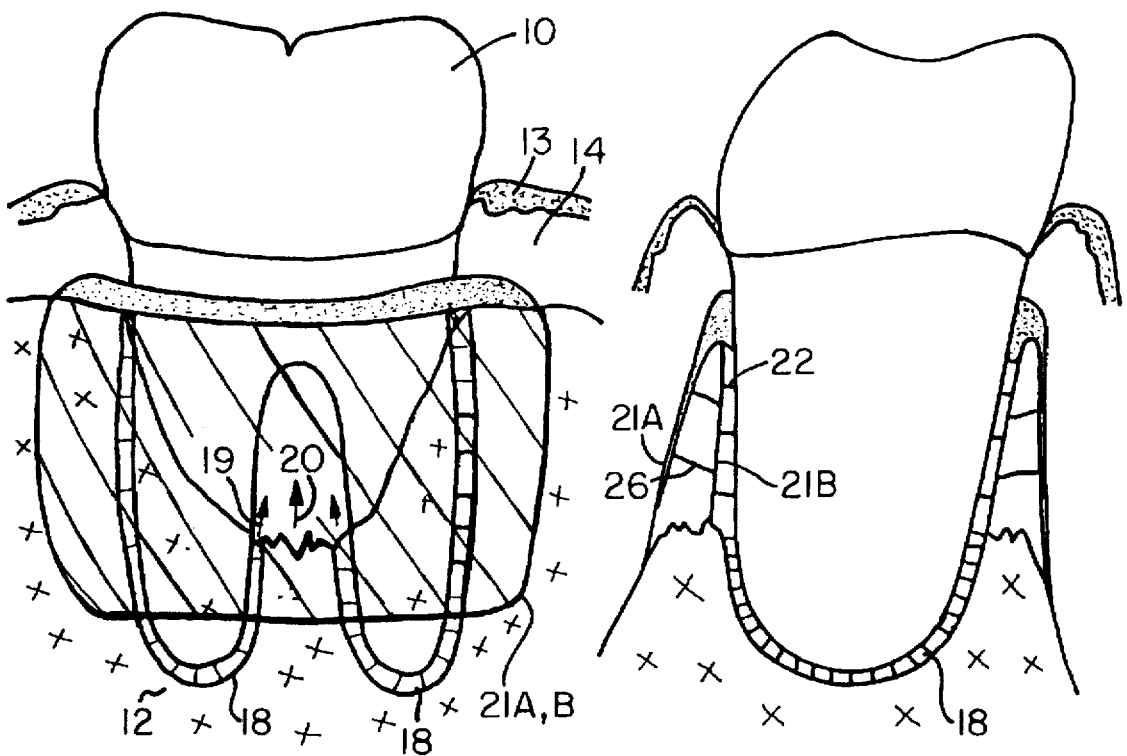
FIGS. 19 and 20 are views similar to FIGS. 17 and 18 illustrating the third embodiment of the present invention as in FIGS. 10–12, applied to a two-rooted tooth.

FIGS. 17 and 18 show a two-rooted tooth with a so-called bifurcation defect, i.e., a destruction of the tooth-supporting tissue (periodontal ligament and bone) between the two roots of the tooth. The element 21 is applied to cover the entrance of the bifurcation either on the buccal side or on the lingual side or on both. The spacers 22 maintain the space between the root surfaces of the two roots and the element. The element is glued at the cervical portion 16 to the cervical part of the roots, as previously discussed. Also in this case, the one-layer type of element presented in these figures does not secure a predictable regeneration concerning the bone in relation to the periodontal ligament. There is, therefore, a certain risk of undesirable bone regeneration in direct contact with the root surface (ankylosis). To make sure that unpredictable healing is avoided, the element can be modified according to FIGS. 19 and 20 which illustrate the same type of tissue destruction as in FIGS. 17 and 18, but with an element that has an outer portion 21A and an inner portion 21B. The latter portion is close to the surface of each of the two roots but kept a predictable distance from those surfaces by spacers 22. The element portion 21B is connected to the outer element portion 21A by means of other spacers 26 which keep the two element portions in a predetermined relation to each other. These structures can also serve as a skeleton for the regeneration of bone cells and bone tissue. An alternative is to use threads forming a three-dimensional mesh as a scaffold for the regenerating tissue.

It should be noted that one or the other layer of the double-layer elements described above can be used alone depending on the location and character of the defect to be healed.

In summary, embodiments of invention comprising two sheet-like portions are depicted in FIGS. 4–6, 10–12, 15–16 and 19–20. The article is adapted for selectively-guided tissue regeneration in the treatment of a periodontal defect adjacent to a root of a tooth. The article comprises an element comprising a first sheet-like portion 21A and a second sheet-like portion 21B. The first portion 21A is adapted to be disposed substantially vertically at the site of such defect, and has a first surface adapted to face towards the root of the tooth, and an outer surface. The second portion is adapted to extend laterally away from said first portion, and has an under surface.

The first surface of such first portion has associated with it a first spacing means, in the form of short protrusions or bosses 22 serving as spacers. The spacers comprising the spacing means have a free end and extend laterally inwards towards the root. The free end of such short spacing member is adapted to be placed in contact with the outer surface of the root, whereby the article is adapted to maintain the first surface of such first portion at a fixed distance from the root, thereby forming a space between the root and the first surface of such first portion. That space is adapted to discriminate between the growth thereinto of periodontal ligament tissue and the growth thereinto of bone tissue.

The second portion is joined to the first portion at the coronal edge of the latter. The second portion has a length extending away from such first portion to beyond such defect and is adapted to have its under surface be disposed adjacent to normal bone tissue. The plane of the second portion forms an angle, when said element is so disposed adjacent to the tooth, with the plane of such first portion, with the angle being in the range of from about 20 to about 90 degrees.

Such an article may also comprise a second spacing means, adapted to maintain the under surface of the second portion at a spaced distance from the opposing surface of the first portion. The second spacing means comprises at least one secondary elongated spacing member, such as spacer 26. A plurality of such second portion secondary spacing members may be employed. The length of at least one of them may be less than any other secondary spacing member, as depicted in FIG. 12. They may depend from the second portion, extending laterally toward the opposing surface of the first portion.

The article may comprise a combination of said secondary spacing members affixed to or integral with the under surface of such second portion, extending generally laterally away from the under surface thereof and have non-affixed outer ends adapted to contact the opposing surface of such first portion, as in FIG. 12.

The article may be adapted to be positioned tightly adjacent to said root near the coronal end thereof.

Either portion of the article may be perforated.

The article may be biodegradable and/or comprise at least one biofunctional substance.

The invention also includes a method of providing selective influence on tissue regeneration in the vicinity of a periodontal defect, which method comprises the steps of (a) separating soft tissue from at least a portion of the surface of a root of a tooth located at such a defect, which portion is located adjacent to the defect, and (b) affixing to such root surface an embodiment of the article as described above, such embodiment being affixed near or slightly apical to the cervix of the root, and tightly affixing the article to prevent the growth in an apical direction of soft tissue along the surface of the root.

Embodiments of the invention comprising a single sheet-like portion are depicted in, for example, FIGS. 7–9, 14, and 17–18. The article also is adapted for selectively-guided tissue regeneration in the treatment of a defect in the bone adjacent to a root of a tooth. This article comprises an element comprising a sheet-like portion 21 having a coronal edge and an apical edge, and having a first surface adapted to face generally towards the root of a tooth. The portion has sufficient length and is adapted to have its apical edge disposed adjacent to the normal bone tissue and underneath any connective tissue normally overlying such normal bone tissue.

The element further comprises at least one spacing member having a free end that is affixed to its first surface and underneath any connective tissue normally overlying such normal bone tissue. The spacing members extend generally laterally inwards towards the root, with their free ends being adapted to be placed in contact with the root, whereby the first surface facing the root is maintained at a distance from the root. This design forms a space between the root and the first surface that is adapted to permit the growth thereinto of periodontal ligament tissue and new bone tissue.

The article can be adapted to be disposed generally vertically at the site of a defect. It may also be adapted to be positioned tightly adjacent to the root near the coronal end thereof.

In a modification of the article, the apical edge is adapted to be firmly disposed against healthy bone tissue at a location outwardly of the periodontal ligament and where the surface of said healthy bone tissue is sloping apically and inwardly.

The article may be biodegradable and/or comprise at least one biofunctional substance.

The invention also includes a method of providing selective influence on tissue regeneration in the vicinity of a periodontal defect, which method comprises the steps of (a) separating soft tissue from at least a portion of the surface of a root of a tooth located at such a defect, which portion is located adjacent to the defect; and (b) affixing to such root surface an embodiment of the article as described above, such embodiment being affixed near or slightly apical to the cervix of the root, and tightly affixing the article to prevent the growth in an apical direction of soft tissue along the root's surface.

Figure 22:
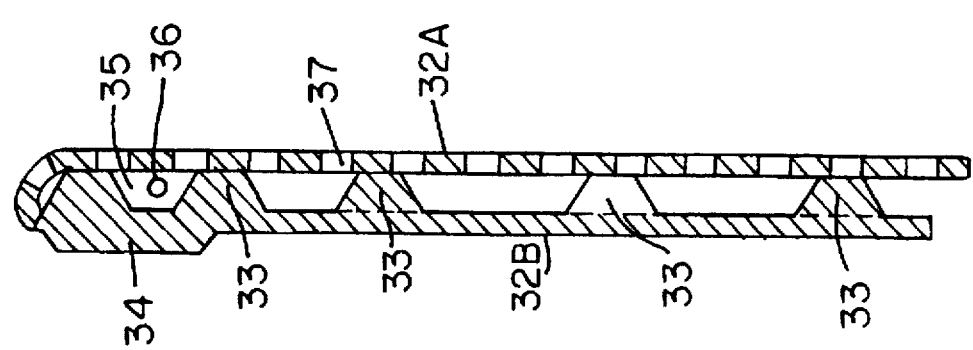
FIG. 22 is a vertical-sectional view of the element of sandwich structure obtained by using the sheet of FIG. 21.
Figure 21:
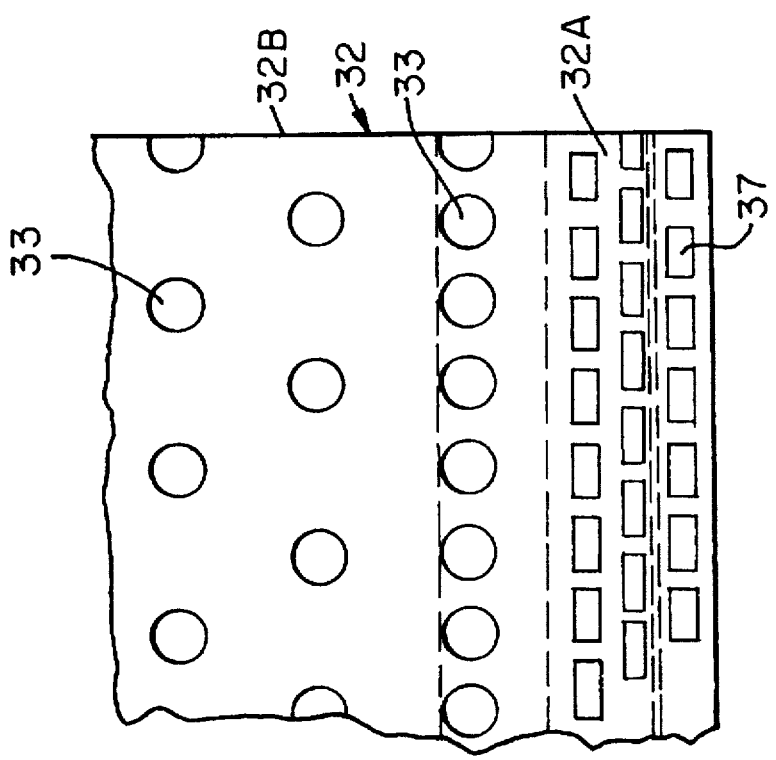
FIG. 21 is a fragmentary plan view of a sheet for an element of sandwich structure.

FIGS. 21 and 22 disclose an embodiment of the present invention which forms a sandwich-type structure made of a sheet 32 of a rectangular or other configuration having two substantially equal portions 32A and 32B shown fragmentarily only in FIG. 21. This sheet is a foil made of a biodegradable polymer material having a thickness, e.g., of about 120–150 μm, and a size, e.g., of about 10×20 mm. However, the shapes, configurations and dimensions can vary as can the stiffness of the material. The single sheet can have a thickness from 10–20 μm up to 500 μm. The stiffness can vary from a non-flexible, centrally located core to a completely flexible consistence of the peripheral parts. The different configurations may include ovoid, horseshoe shaped, or skirt shaped foils.

The sheet can be produced by compression molding, but other manufacturing methods can be applied, such as calendaring, casting, molding, or other techniques. Portion 32B forms at one side thereof protrusions 33 which have the shape of truncated cones with a base diameter of about 0.4 mm and a height of about 0.2 mm. The protrusions of one row thereof adjacent to portion 32A have a center distance of about 0.6 mm, with the center distance of the remaining rows being about 1.2 mm and the center distance between the rows being about 1.0 mm. At the top, forming the most coronal part of the element when mounted to a tooth, the portion 32B forms a rib or bar 34 extending over the full width of portion 32B and protruding at both sides thereof, said rib or bar being constructed to be tightly applied against the tooth. The rib or bar 34 defines, together with the adjacent protrusions 33, a channel 35 for an anchoring ligature 36 extending through the channel and being displaceable longitudinally or non-displaceable therein.

FIG. 22 discloses a double-sheet element. In the embodiment shown, the sheet of FIG. 21 has been folded to form a double-sheet structure or a laminate, wherein the adjacent surfaces of portions 32A and 32B are spaced by protrusions 33 formed by the portion 32B, at a distance of 0.2 mm to create a free space between said surfaces.

Figure 23:
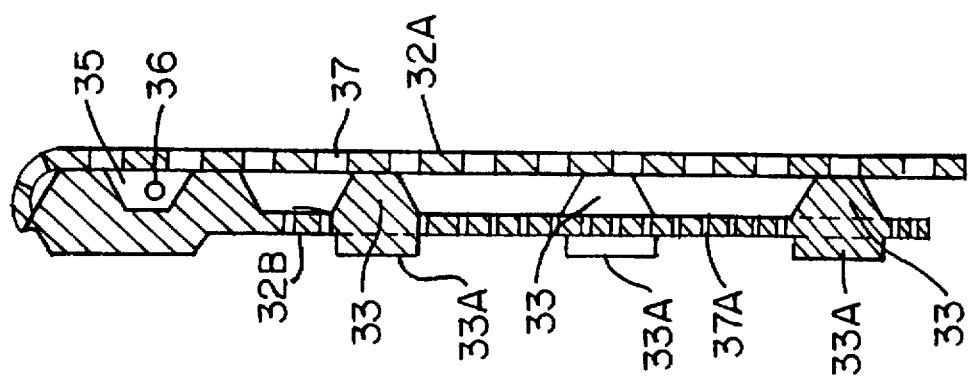
FIG. 23 is a vertical-sectional view of a preferred embodiment of the sandwich structure.

In the preferred embodiment, disclosed in FIG. 23, the portion 32B forms at the outside surface thereof protrusions 33A distributed over the surface in the same configuration as protrusions 33 and having a height of about 0.1 mm. These protrusions are provided to form spacers between the outside surface of portion 32B and the surface of the tooth. Moreover, there are provided small circular perforations 37A having a typical diameter of 70 μm and arranged in a hexagonal pattern, wherein the center distance of the apertures is about 0.2 mm. These apertures cover an area of about 15 percent of the surface area. The total thickness of the element of FIG. 23 should, preferably, be of the order 500–550 μm.

The two portions 32A and 32B can comprise individually produced separate sheets which are interconnected at one or more edges and/or at the protrusions 33 to form a sandwich structure or a laminate. Moreover, the protrusions 33 can be replaced by other means forming the spacers such as biocompatible materials or combinations of materials with variable degrees of degradation to govern the degradation profile and thereby the ingrowth pattern of tissues. As an example, quickly biodegradable materials such as hyaluronic acid might be blended with more slowly biodegradable polyactide (PLA) components.

Figure 24:
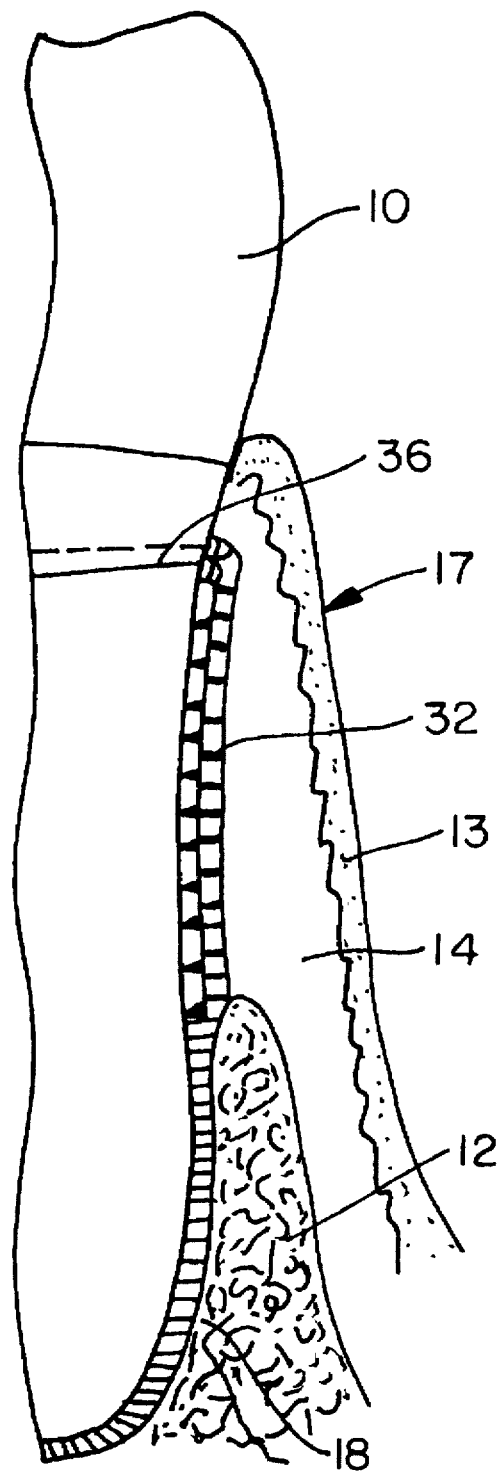
FIG. 24 is a fragmentary vertical-sectional view of a tooth with the element of the sandwich structure shown in FIG. 23 mounted on the tooth.

FIG. 24 discloses the element of FIG. 23 mounted to a tooth. An incision is made and a mucoperiosteal flap is raised to expose the bone having a defect to be regenerated. It is desirable that the coronal part of the element is placed about 2 mm apical to the gingival margin, following suturing of the flap, in order to facilitate connective tissue ingrowth into the element before it is reached by the apically proliferating gingival epithelium. This will prevent gingival recession and element exposure. However, the position of the anchoring ligature 36, used to attach the element to the tooth, is also determined by the highest point of the alveolar bone level around the tooth. This means that it is not possible to place the coronal aspect of the element apical to this level. As a consequence, it is desired to have the ligature placed as close as possible to the top of the element in order to facilitate optimal flap coverage of the element. This is achieved in the embodiments of FIGS. 21–23, wherein channel 35 and, thus, ligature 36 is located in the most coronal portion of the element. The ligature can be longitudinally displaceable in the channel, which is a convenient feature in the implantation situation, allowing the element to be easily adjusted to the desired position. However, the ligature can also be attached to the element in a fixed position. A further advantage inherent in the ligature channel is that it facilitates the placement of two elements, if desired, on a tooth with the same ligature. It also provides the option of, at the point of surgery, separating a part of an element from the rest with the purpose of placing this separated part on another location of the treated tooth in question. Such separation may also facilitate intra- and supra-defect application of the element inside the defect, and application of the element laterally to the defect, respectively. The rib or bar 34 aims at sealing the coronal margin of the element to the root surface to prevent gingival tissue downgrowth between the element and the root surface. As this bar is located in the region of the ligature channel, it also serves as reinforcement to prevent rupture of the device via the anchoring ligature.

Central to the periodontal application of the guided tissue regeneration concept is the prevention of gingival connective tissue and epithelium making contact with the root surface during healing. The sandwich structure of FIG. 23 is ideally suited to accomplish this objective. During the healing process after the element has been implanted, gingival connective tissue will easily penetrate the proportionally large rectangular perforations 37 of the external layer 32A, facing the gingival flap, and then spread out in the space between the two layers 32A and 32B. A biological "element" is thus formed that prevents downgrowth of gingival epithelium along the wound surface facing the element. As a consequence, gingival recession and element exposure are prevented. The outcome of the competition between apical migration of the gingival epithelium and connective tissue ingrowth into the sandwich structure will, to some extent, be dependent upon the distance the epithelium has to migrate before reaching the coronal aspect of the element. This means that, during initial healing, minor epithelial downgrowth may sometimes occur at the most coronal part of the wound preceding the connective tissue ingrowth. However, since connective tissue ingrowth is permitted through the perforation of the entire length of the external wall, the epithelial migration will always be prevented somewhere along the extension of the element.

Conventional devices for guided tissue regeneration often collapse into close contact with the treated root surface after implantation, thus blocking the space between the root and the device that is desired for ligament regeneration. The spacers 33A on the internal layer 32B prevent any such collapse, thereby assuring the space needed for the regeneration of the periodontal ligament.

Figure 25:
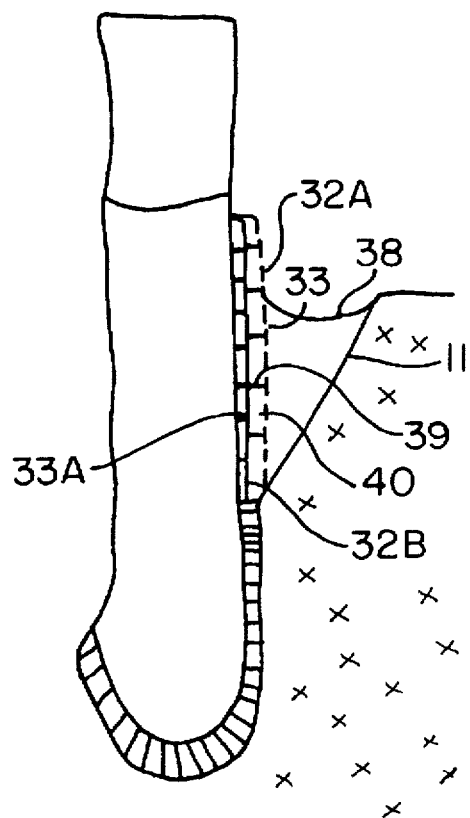
FIG. 25 is a view similar to FIG. 12 of a modified element of sandwich structure.
Figure 26:
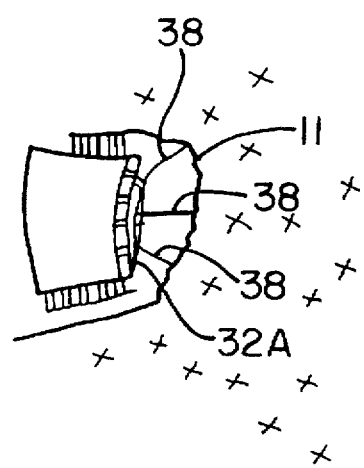
FIG. 26 is a plan view of the arrangement in FIG. 25.

A further development of the sandwich element of FIG. 23 is disclosed in FIGS. 25 and 26. In these figures, which disclose the periodontal tissue regeneration using an element with intra-defect application, the element is placed alongside the root surface and is placed against the tooth to support said element in the intended position by means of anchoring pins 38 which have some springiness so that they can be pressed into the bone defect 11 to span under tension the distance between the element and the defect wall. Before placement, the element is trimmed to fit the borderlines of the defect along the root surface. This is, preferably, made by punching a separate foil to cover the root surface of the defect. The element is then trimmed according to the borderline impressions of the foil to fit the margins between the defect and the remaining periodontal ligament. The pins may be replaced by a wedge or a body filling the bone defect. In the embodiment of FIGS. 25 and 26, the protrusions of FIGS. 21 to 23 are replaced by ribs 39 extending substantially in the horizontal direction so that the space between portions 32A and 32B of the sandwich structure is divided into a number of individual compartments 40 forming undercut cavities, to which the surrounding tissue has access through the perforations 33. The spacers 33A secure enough space for ingrowth of periodontal ligament to cover the root surface facing the defect, at the same time guiding the other tissues to form outside the element. This method presupposes a biodegradable material. The intra-defect application according to this description means that it is also very easy to cover the element with a flap in situations where it is difficult to mobilize a flap for complete coverage. This, in turn, means that it should be easier with this method to achieve a closed environment optimizing the wound healing process. This placement of the element might be preferred when there is need for gingival tissue recover of denuded root surfaces. Another preferred indication is periodontal regeneration at the surface of a tooth root facing an adjacent extraction socket.

In summary, the sandwich-type embodiments of the invention are depicted in FIGS. 21–25. The article is adapted for selectively-guided tissue regeneration in the treatment of a periodontal defect adjacent to the root of a tooth.

The article comprises a first sheet-like portion and a second sheet-like portion, the first portion having a first surface adapted to face towards the root, an outer surface, and a coronal end and an apical end. The first portion is adapted to be disposed adjacent the root at the site of such defect.

The second portion has an inner surface and an outer surface, with the inner surface being opposite and essentially parallel to the outer surface of the first portion. At least one of such portions comprises a plurality of perforations.

The element further comprises a first spacing means located between the outer surface of the first portion and the inner surface of the second portion, with such first spacing means being adapted to maintain the first portion and the second portion in essentially parallel relationship, thereby creating a first space that is adapted to permit ingrowth of new connective tissue thereinto through such perforations.

The article further comprises a second spacing means that is adapted to create and maintain a second space between the root and such first surface, with the second space having sufficient width perpendicular to the longitudinal axis of the root to permit ingrowth thereinto of periodontal ligament tissue.

The article may further comprise tightly applying means adapted to permit the coronal end of the inner surface of the first portion to be tightly applied to the surface of the root. Such a tightly applying means may comprise a hollow channel extending across the width of the first portion near its coronal end. Such a channel is adapted to have disposed therein an anchoring ligature that is adapted when under tension to compress such inner surface tightly against the surface of the root. The ligature may be displaceable longitudinally in the channel.

The stiffness of the first portion and/or the second portion may vary.

The spacers of the first spacing means may have the shape of a truncated cone. The spacers of the second spacing means may have a rectangular cross-section, and these may be located in a uniform pattern. Both such features may be employed in the same article. A majority of the first spacers and the second spacers may be centered opposite one another.

Such perforations may be in the second portion, and may be rectangular. Such perforations alternatively may be in the first portion, and may be circular. Optionally, both of such portions may have a plurality of perforations. The cross-sectional area of individual perforations in the first portion may be uniform, and also may be smaller than the cross-sectional area of individual perforations in the second portion.

The first portion and the second portion may be integral.

At least one of the first spacing members may comprise a portion of the hollow channel.

The first portion may further comprise a rib extending longitudinally across the width of the inner surface of said first portion near the coronal end thereof, such rib defining a portion of the outer boundary of the hollow channel.

The coronal end of the first surface of the first portion may comprise a rib extending across the width of the first surface of the first portion, which means is adapted to be, in use, positioned against the surface of the root slightly apical to the cervix of said tooth. Such a coronal spacing means may be continuous.

The element may be biodegradable, and/or comprise at least one biofunctional substance.

Such an article may be employed in a method of providing selective influence on tissue regeneration in the vicinity of a periodontal defect. The method comprises the steps of (a) separating soft tissue from at least a portion of the surface of a root of a tooth located at a defect, which portion comprises that area of the root surface located adjacent such defect; and (b) affixing to said root surface an article as described above, with the article being affixed near or slightly apical to the cervix of the root, and tightly affixing the article to prevent the growth in an apical direction of soft tissue along the root's surface.

The method is also suitable for providing selective influence on tissue regeneration in the vicinity of a periodontal defect, a bone defect or an implant. Such method comprises the steps of separating soft tissue from at least a portion of the surface of bone tissue at the site of such defect or implant, which portion comprises that area of the surface of bone located adjacent the defect or implant, and disposing at or near such surface an article as described above.

FIGS. 22–23 depict a feature of the invention that comprises the structure for tightly adhering an article to solid tissue, such as a tooth, including a root thereof, or a bone or an implant, and is also referred to above. A rib or bar forming a part of the structure of the article extends at least part of the way around such tissue and forms a channel that is closed over at least part of the width of the article. A ligature is disposed in the channel, and optionally may be displaceable longitudinally along the channel. When under tension, the ligature is adapted to tightly adhere at least part of the article to the solid tissue.

Figure 27:
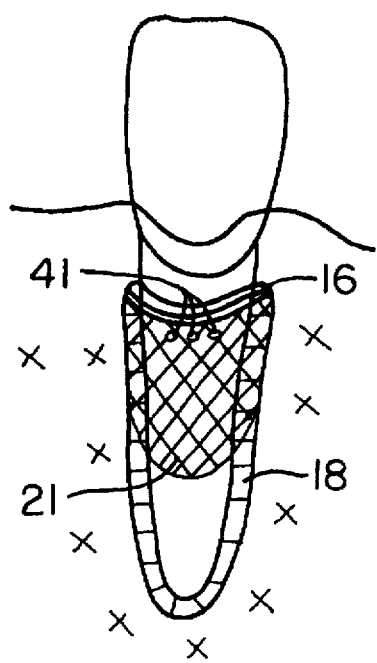
FIGS. 27 and 28 are views similar to FIGS. 7 and 9 of a still further embodiment of the present invention.
Figure 28:
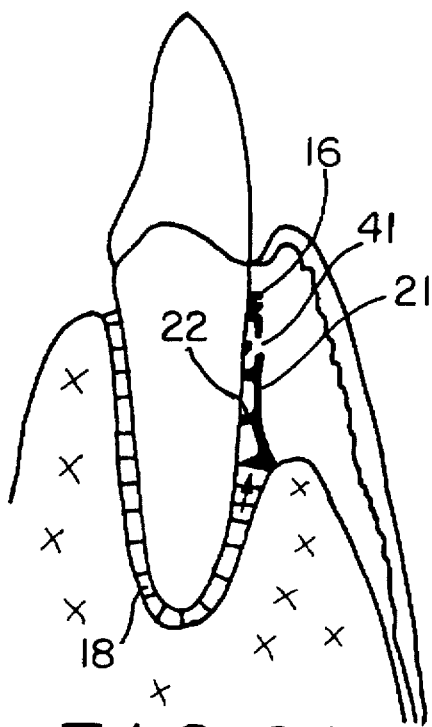

In FIGS. 27 and 28 there is disclosed a single element 21 of the type shown in FIG. 9. This element has spacers 22 at the side thereof facing the tooth, and a cervical portion 16 which is attached to the tooth. The element is impervious except that there are provided in the upper portion thereof, adjacent to the cervical portion 16, three central perforations 41, which thus are remote from the side edges of the element and also from the front of the periodontal ligament tissue 18. These perforations should be dimensioned such that the penetration of cells from surrounding tissue is retarded or delayed, but an unobstructed growth of tissue through the element is prevented, since this would spoil the purpose of the element. The perforations allow oxygen and nutrition to reach the space between the element and the tooth, which may stimulate the growth of desired tissue in the cervical region into said space, so that the space will be substantially filled by such tissue before growth of undesired surrounding tissue into the space between the element and the tooth through the perforations has started.

Perforations, of the type mentioned above, may also be provided in an element such as element portion 21B in FIG. 6. In that case, the perforations should be located near the wall of the bone defect.

Figure 29:
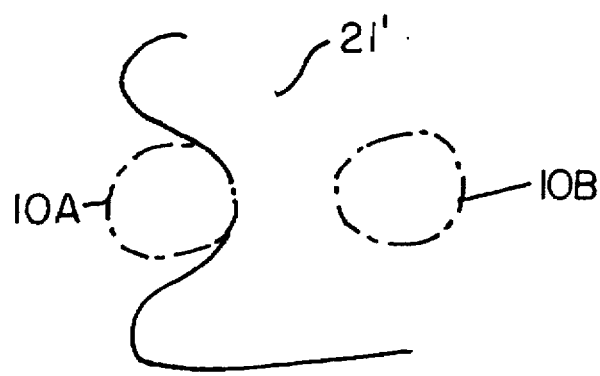
FIG. 29 is a plan view of an element to be used between two adjacent teeth.

A preferred embodiment for regenerative treatment of interproximal periodontal defects is a double-curved element 21, as shown in FIG. 29, designed to have a close fit to the proximal root surfaces of two adjacent teeth, as indicated at 10A and 10B by dash-and-dot lines. Measurements of the distance between the proximal root surfaces of adjacent teeth with normal proximal contact relationships show that this distance may vary considerably at the cementoenamel junction, as well as, more apically. The element should, therefore, be designed to have a width which may vary from 1 to 10 mm, preferably, from 3–7 mm, at its most narrow site. However, because of the malleability of the material, this distance can be increased at least between 25 and 50 percent by stretching the element to secure a tight adaptation to the proximal root surfaces in each individual case. This embodiment may include spacers integral with the element, or may be combined with separate spacers to avoid collapse of the element into the periodontal defect. The element can also be reinforced by fibers or ridges or be provided with a harder core to avoid collapse.

Figure 30:
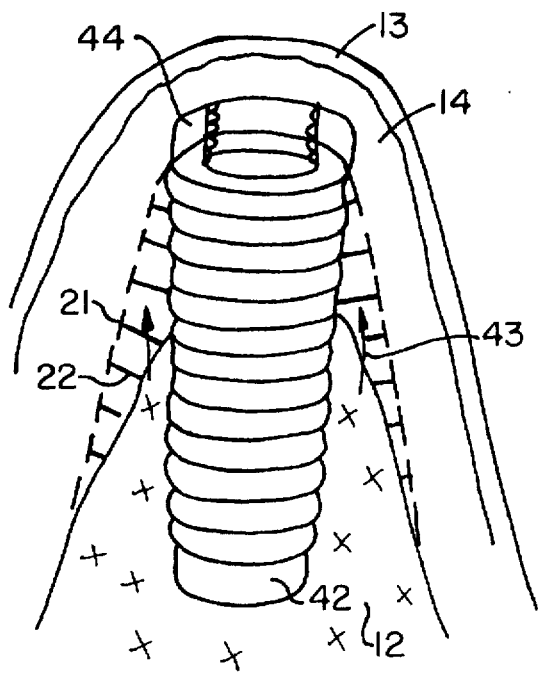
FIGS. 30 and 31 are views similar to FIGS. 1 and 3, illustrating an embodiment of the present invention applied to an artificial screw or similar implant.
Figure 31:
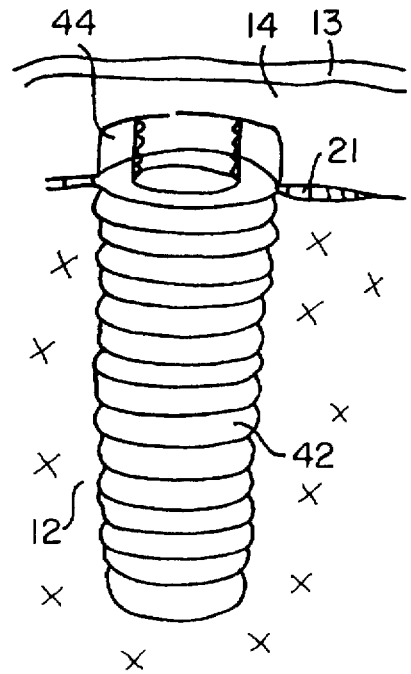

FIGS. 30 and 31 show a cylindrical implant 42 of a biocompatible material. The implant is shown to be of the screw-type, but can be of any other type known in the art. The implant is installed in the bone 12, but, as shown in FIG. 30, the bone covers only the lower half of the implant while the rest of the implant is covered by connective tissue 14 and epithelium 13. A biodegradable or non-biodegradable element 21 covers the upper half of the implant and parts of the bone tissue 12. Spacers 22 maintain a predetermined space for the bone tissue cells to regenerate in superficial direction, as indicated by arrows 43. The bone surface facing the space is, preferably, mechanically traumatized to cause bleeding and expose the subsurface to facilitate the bone growth into the space. The spacers 22 include protrusions or bosses on the element, but can also include threads forming a mesh-like structure serving also as a scaffold for regenerating bone cells and other components. The element components, preferably, are loaded with bone stimulating preparations on the side of the element facing the space, as well as on the spacers or the mesh, respectively. The element may be passively placed or positively retained to the implant using a specially designed screw 44.

This element may also vary greatly in shape, design/configuration, and stiffness. Thus, it may consist of one layer with a stiff, centrally-located core and a less stiff (more malleable) peripheral part. The stiffer core is designed to maintain space (i.e., not collapse). The peripheral part is designed to adapt to the topography of the bone surface surrounding the defect. The different degrees of stiffness can be achieved by matching the softness of the material of the element and the thickness of the element. The more malleable, peripheral part of the element should be reinforced with ridges, or the like, to support spacers which are also peripheral to the defect (possibly occupied by an implant), to create and maintain space for ingrowth of bone via the surgically created perforations of the cortical bone lateral to the defect.

The single-layered element, preferably, is supplied with undercut cavities to increase the stability of the wound area by contributing to the retention of the flap. In addition, these cavities create an extremely thin wall of material in the bottom of the impression. The thin bottom of the impressions will break down much faster than the rest of the material (without causing too early perforations), thereby speeding up the overall break-down of the element.

In another embodiment, there may be two or more layers in the element with perforations in one or several of these layers located strategically so that the distance for the ingrowing connective tissue cells will be as long as possible. The perforations of the inner layer should, thus, be located as peripheral as possible in relation to the cavity, preferably, even peripheral to the surgically made bone perforations.

It should be observed that a combination of cavities and a few perforations might be preferable. If the perforations are strategically placed, the need of transportation of exudate-borne components to the bone defect via the perforations will be fulfilled, and at the same time, the distance the soft tissue cells have to migrate will be maximized.

Still another way of delaying the ingrowth of soft tissue cells to the bone defect is to reduce the space between the layers so as to substantially delay or even totally prevent the ingrowth of soft tissue cells via the perforations of the element.

The different layers might also be constructed to have different stiffness instead of supplying each layer with a hard central core. Thus, a relatively stiff inner layer with a smaller diameter is designed to cover the defect, including the edges of the bone surrounding the defect. This layer is supplied with spacers to create space also above the bone edges. A larger and softer outer layer covers the inner layer and extends peripheral to the inner layer having spacers except in the peripheral part which is folded over the edge of the inner layer to prevent soft tissue ingrowth.

Figure 32:
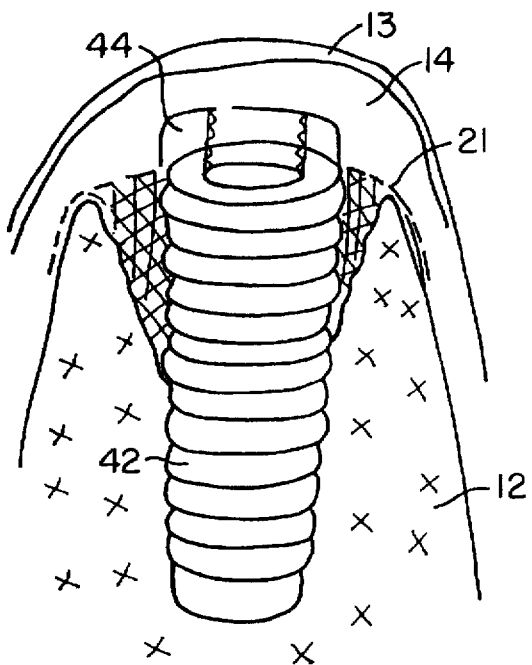
FIGS. 32 and 33 are views similar to FIGS. 30 and 31, illustrating a second embodiment of the present invention applied to an implant.
Figure 33:
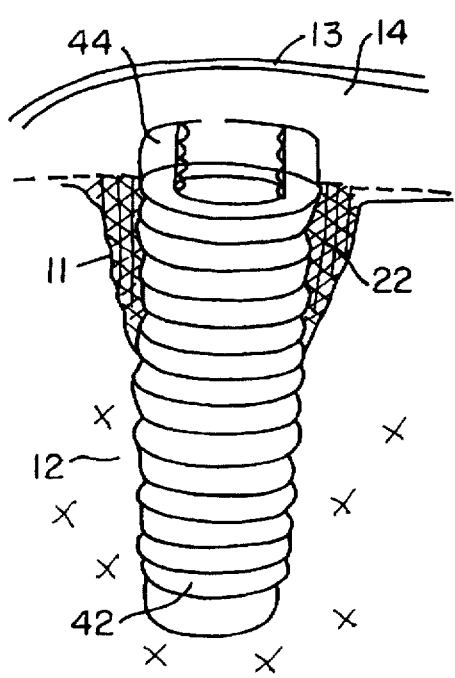

FIGS. 32 and 33 illustrate the application of the same type of element as in FIGS. 30 and 31, but with the element covering a bone defect 11 which is defined between the implant wall and the alveolar bone, the element covering the upper (superficial) entrance of the defect.

Figure 34:
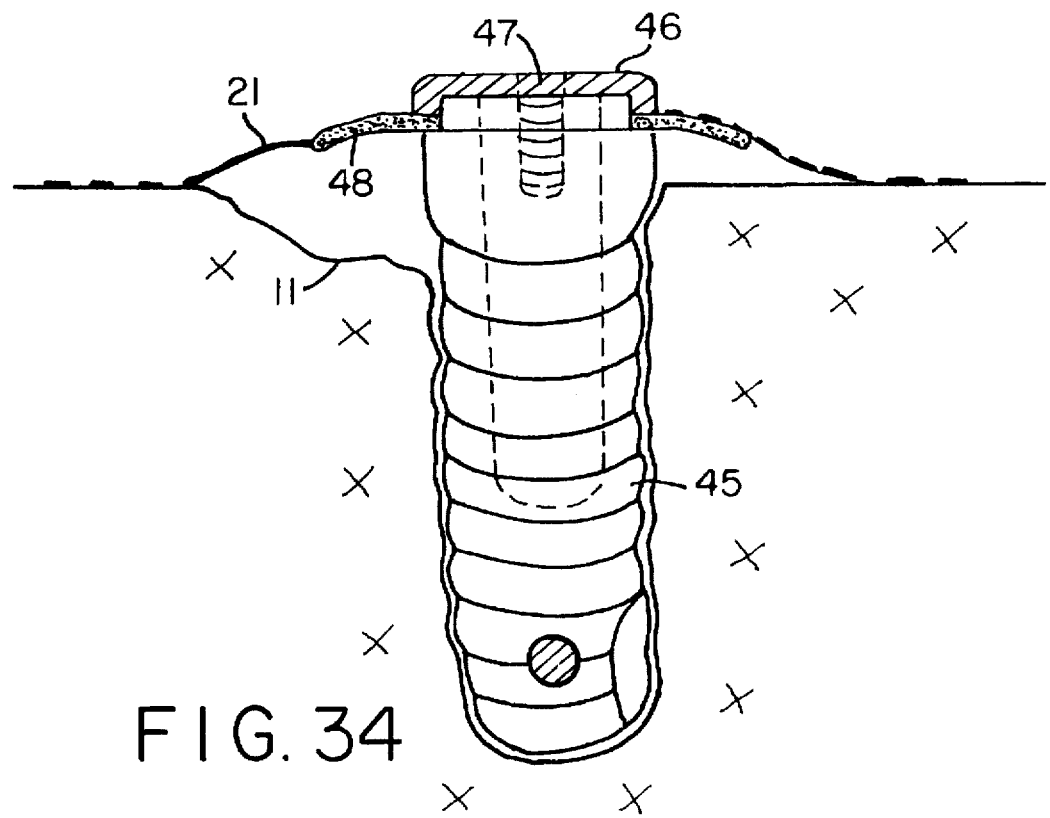
FIG. 34 is a view similar to FIG. 30, illustrating a third embodiment of the present invention applied to an implant.
Figure 35:
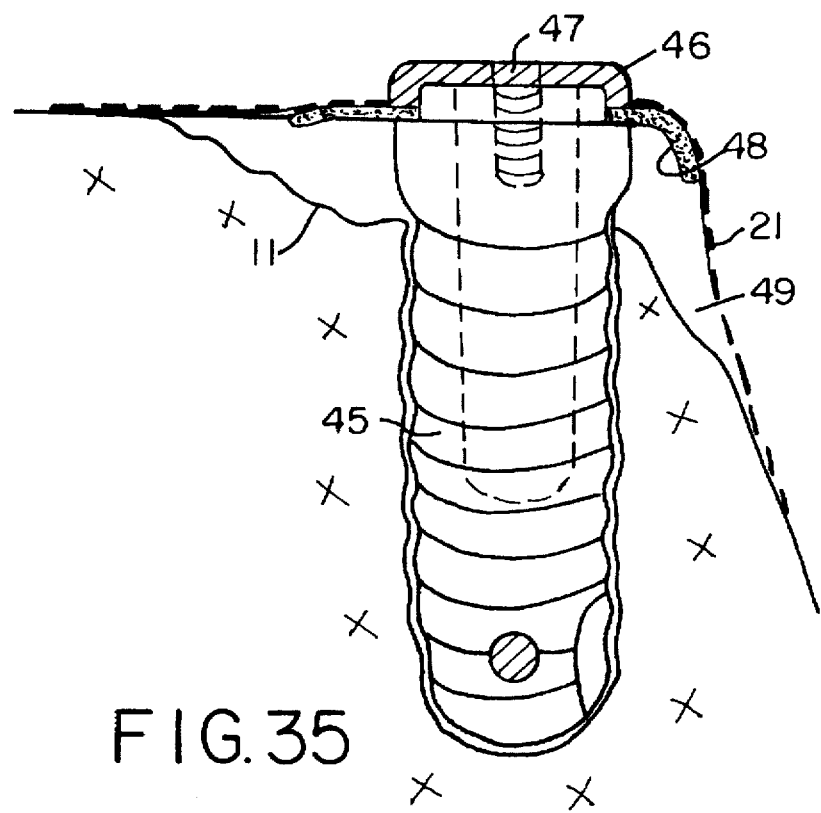
FIG. 35 is a view similar to FIG. 30, illustrating a fourth embodiment of the present invention applied to an implant.

FIGS. 34 and 35 disclose further embodiments of the present invention in connection with an implant 45. In these embodiments, the element 21 is clamped between a cap 46, which is secured into the implant end surface by means of a screw 47, screwed into the implant, together with an underlying member 48, which may be formed as a disc, a net, a star, or a spider. This member is stiff enough to support the element, so that it will be held spaced from the bone 12 covering a bone defect 11. Member 48 may be made of metal, or plastic material which can be plastically deformed at room temperature or at an elevated temperature, so that it may be adapted to the desired form of the element as shown to the right in FIG. 35, wherein member 48 has been bent down so that the element extends substantially vertically to cover a space 49 to be restored by bone tissue growth thereinto.

In summary, embodiments of the invention adapted for use adjacent to dental implants are depicted in FIGS. 30–35. The article is adapted for selectively-guided tissue regeneration around a dental implant, such an implant having an outer side surface and a coronal end. The article comprises an element comprising a sheet-like portion having a first surface and an opposing surface, and a first edge and a second edge. The element is adapted to be disposed whereby such first surface faces towards the implant or healthy bone tissue, with the first edge being adapted to be disposed adjacent to, and at or shortly apical from, at least a portion of the outer side surface of the implant at its coronal end. The sheet-like portion has sufficient length between its first and second edges whereby the second edge is adapted to be disposed adjacent to normal bone tissue.

At least a part of the first surface and the second edge may extend radially outwardly from the implant. Also, at least a part of the first surface nearest the implant may initially extend outwardly from the implant, and then extend apically relative to the implant.

The article may further comprise at least one spacer member, affixed to its first surface, having a free end adapted to be in contact with the outer surface of the implant or of healthy bone tissue, thereby forming a space adapted to permit the growth thereinto of bone tissue. The free end of such a spacer member may be adapted to be in contact with said healthy bone tissue.

The element may optionally be adapted to be secured to the coronal end of the implant by a cap affixable to the implant.

The article may be biodegradable, and/or comprise at least one biofunctional substance.

Such an article may also be employed in a method of providing selective influence on tissue regeneration in the vicinity of a dental implant. The method comprises the steps of separating soft tissue from at least a portion of the surface of bone tissue at the site of the implant, which portion comprises that area of the surface of bone located adjacent said implant, and then disposing at or near that surface an article as described above.

The method is suitable for use in the vicinity of a dental implant. An article as described above is sufficiently tightly affixed to the implant near its coronal end to delay the growth in an apical direction of soft tissue along the surface of the implant.

Figure 36:
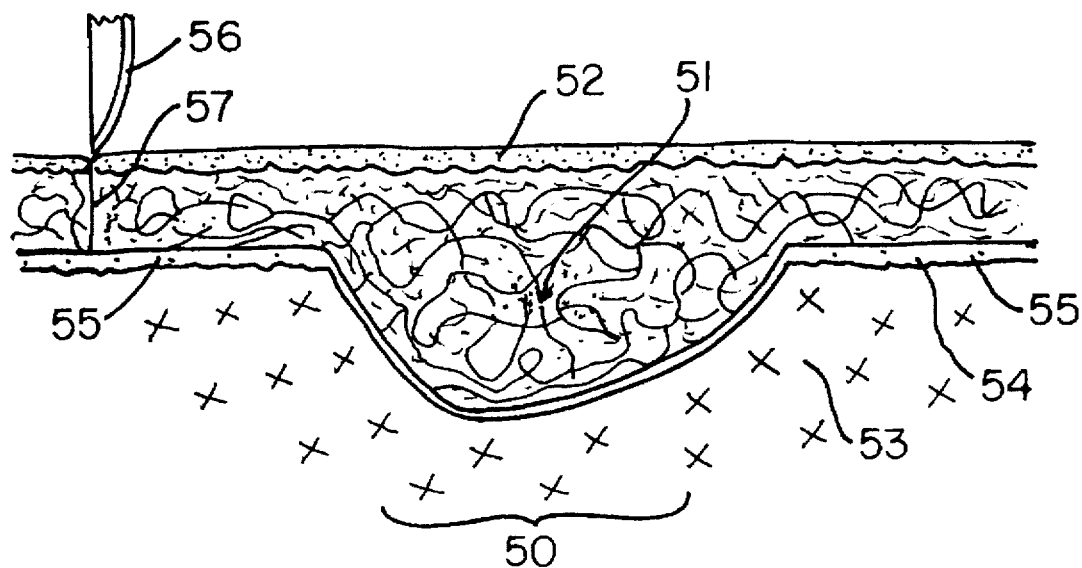
FIG. 36 is a cross-sectional view of a bone defect filled with connective tissue.
Figure 37:
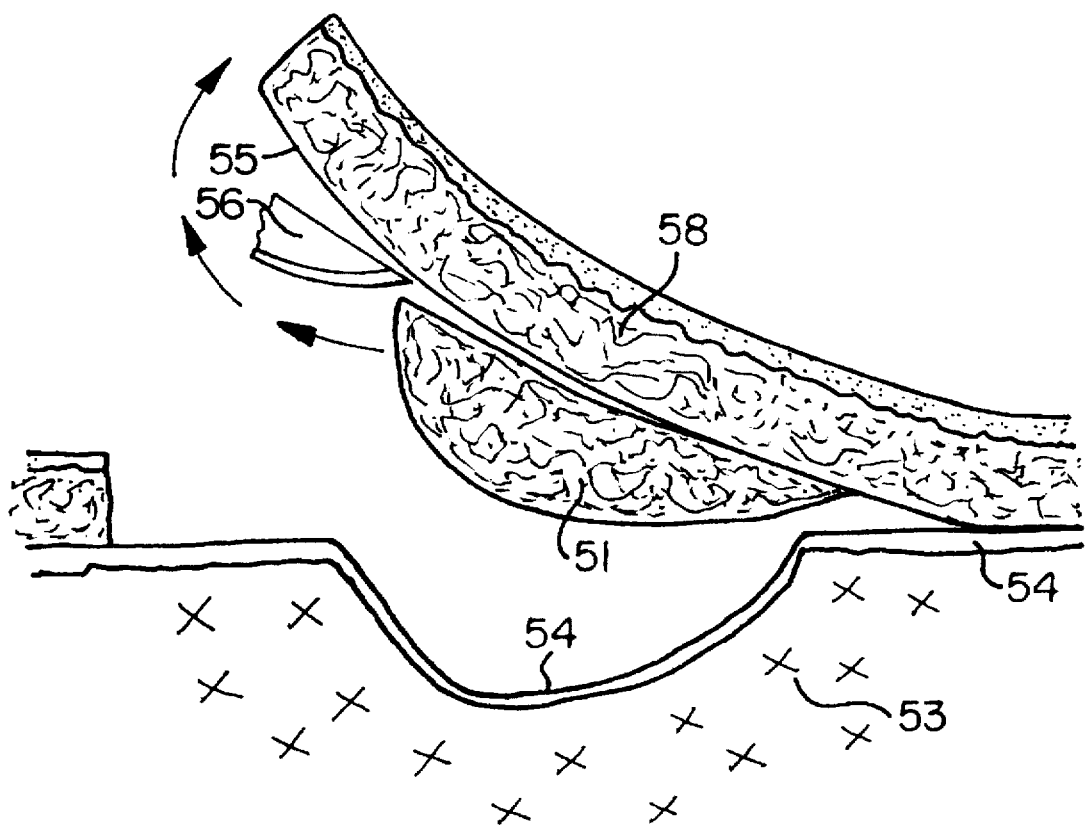
FIG. 37 is a cross-sectional view of the defect in FIG. 36 after a flap has been raised and the connective tissue within the bone defect has been separately removed.

FIG. 36 shows a cross-sectional view of the center of a bone defect or a bone cavity 50 filled with soft (connective) tissue 51 in turn being covered by epithelium 52. The spongious or cancellous bone surrounding the bone defect is indicated at 53 and the compact or cortical bone which covers the spongious bone and demarcates this bone from the soft tissue is indicated at 54. The compact bone, in turn, is covered with a thin membrane, the periosteum 55. By the aid of a surgical scalpel 56, an incision 57 is made through the soft tissue, including the periosteum 54, down to the compact bone to raise a mucoperiosteal flap 58 as shown in FIG. 37, which is showing the same view and section as FIG. 36. The flap is trimmed in that the soft tissue occupying the bone defect 51 is cut away from the rest of the flap 58.

Figure 38:
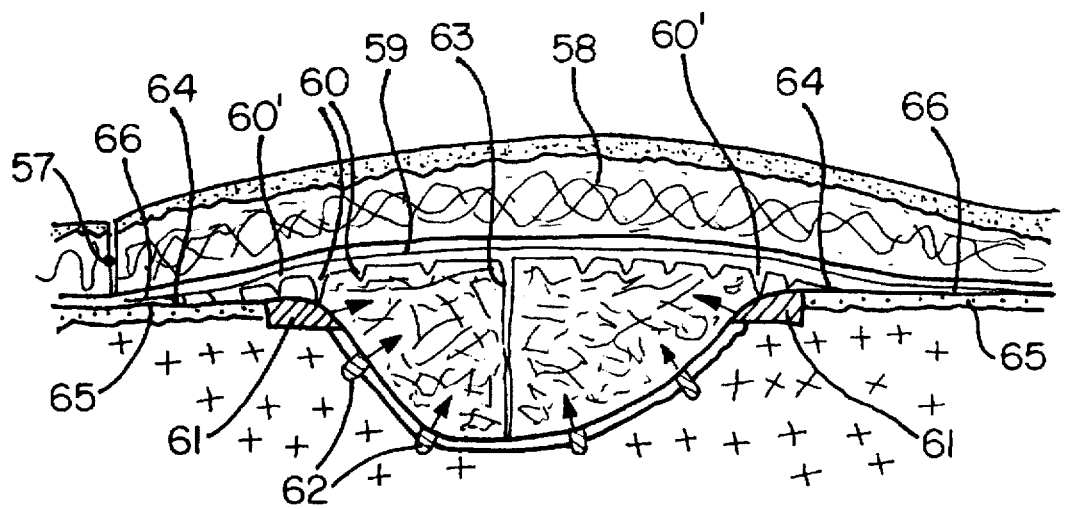
FIG. 38 is a cross-sectional view of the same bone defect as in FIGS. 36 and 37, the element of the present invention being placed to cover the defect and the soft tissue flap being replaced and sutured to cover the element.

FIG. 38 shows the same view and section as shown before in FIGS. 36 and 37, and FIG. 39 shows a horizontal-sectional view of the same defect. An element of the present invention 59 has been placed to cover the bone defect containing a blood clot and bone cells. The element has the form of a plate, sheet, or lamina consisting of a material which, preferably, is bioresorbable. The material might, preferably, be so stiff that the element is able to maintain its shape long enough for the critical guided healing to occur even when it is subjected to loading from the surrounding tissues and the extracorporeal environment. The element is easy to reshape, especially when warmed up. It is provided with protrusions 60 which function as spacers or stand-offs between the plate-formed part of the element and the bone. Those protrusions indicated at 60', which are located in the border line area between the bone defect and the surrounding bone surface, are especially important as they secure a space between the openings of perforations 61, which are made as slots or holes through the compact bone into the spongious bone to secure migration of the bone-producing cells residing in the spongious bone into the bone defect. These perforations are especially important when the bone defect is more or less occupied by an implant, as will be described later on. The slots or holes are made by means of burs, sharp hand instruments, or laser equipment, and should also include perforations 62 of the walls of the defect itself. One or several of the protrusions, indicated at 63, can in certain embodiments of the present invention be very long (5–25 mm) and stiff to assist in the support of the element, especially if the element is made thin and wide and, therefore, is less able to maintain its shape and location without beam support.

A small zone 64 of the element, immediately peripheral to the zone corresponding to the border line perforations, should be in tight junction with the bone surface to prevent ingrowth of connective tissue between the element and the bone which will jeopardize the bone healing of the defect. Peripheral to this occluding zone, the element, preferably, should be so perforated that only a minor part of this area 65 consists of element material, meaning that the connective tissue and/or the periosteal tissue of the flap 58, immediately after the replacement of the flap to cover the element, will come in close contact with the bone surface in a clotting/gluing relationship to secure an attachment with the bone which very soon will be reinforced by ingrowth of cells 66 joining the two types of tissue.

Figure 39:
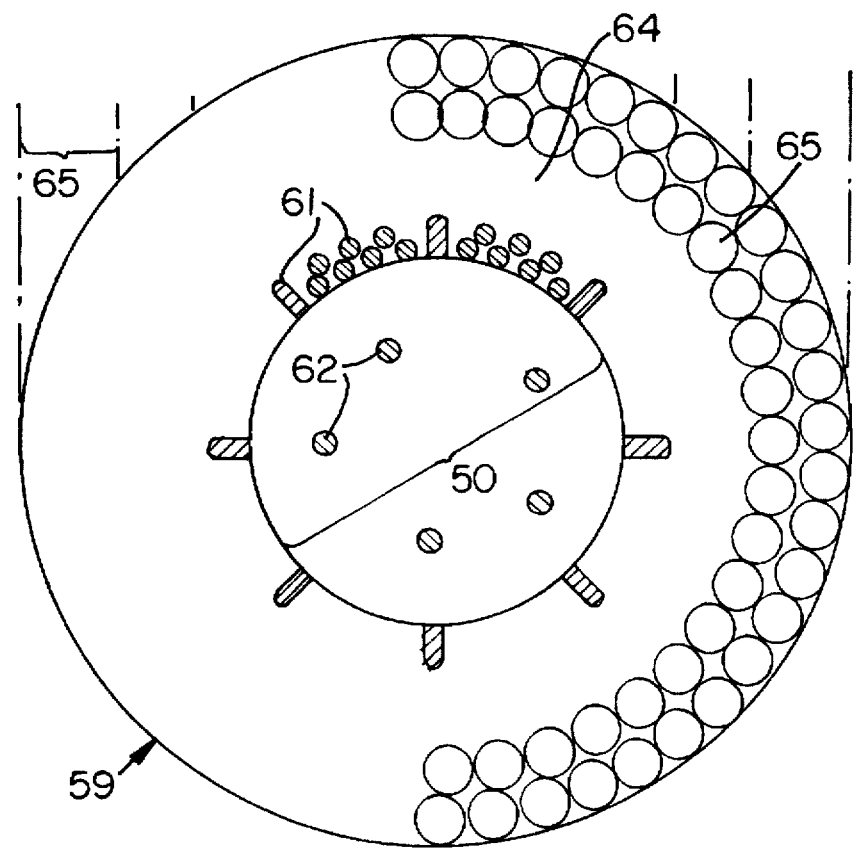
FIG. 39 is a horizontal-sectional view of the same defect.
Figure 40:
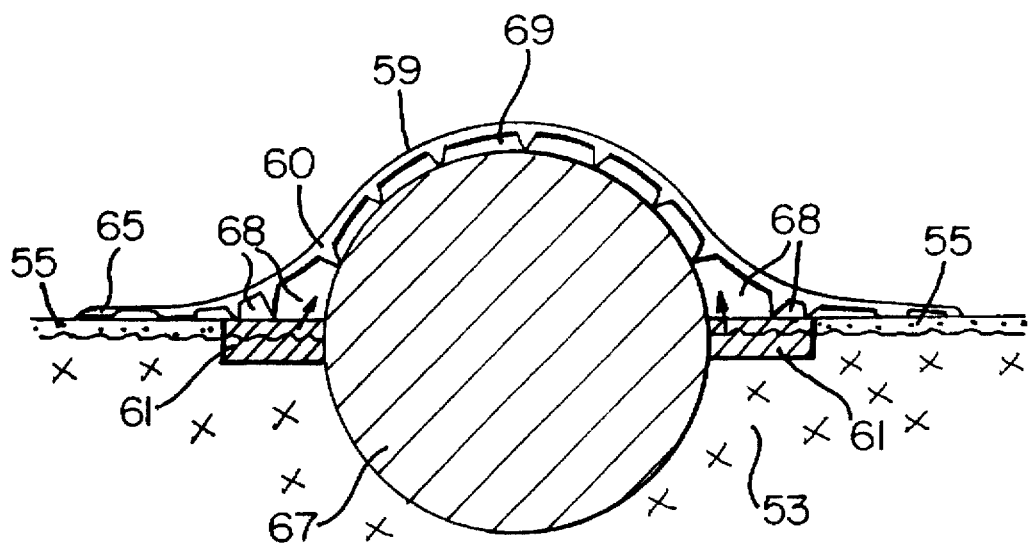
FIG. 40 is a cross-sectional view showing an implant partly located outside the bone tissue.
Figure 41:
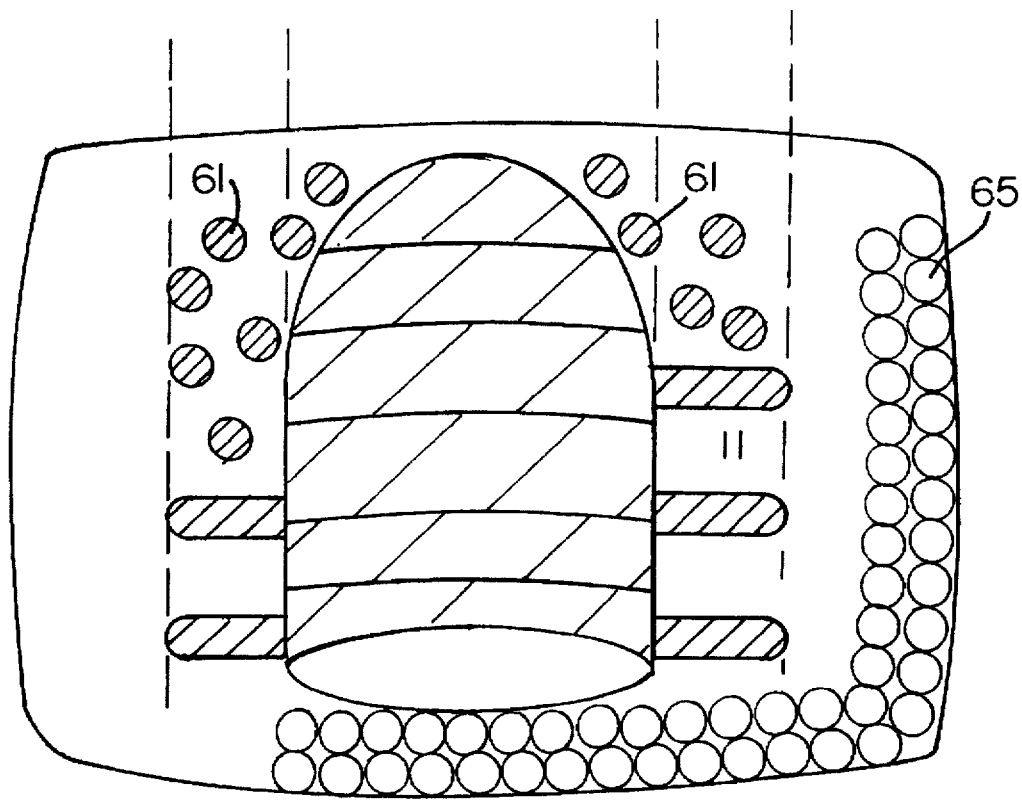
FIG. 41 is a longitudinal-sectional view of the implant of FIG. 40.

FIG. 40 is a cross-sectional view of an implant 67 in part submerged in the bone tissue 53. An element 59, of essentially the same embodiment as described in FIGS. 38 and 39, covers the implant and the bone surrounding the implant. The soft tissue to cover the element is not shown. FIG. 41 is a longitudinal-sectional view showing the denuded part of the implant with the element covering the implant and the surrounding bone. The double role of the protrusions is obvious: first, to create space 68 for the entrance of bone producing cells from the spongious bone area; and second, to create and maintain the space 69 between the element and the implant within which bone is to be formed.

Figure 42:
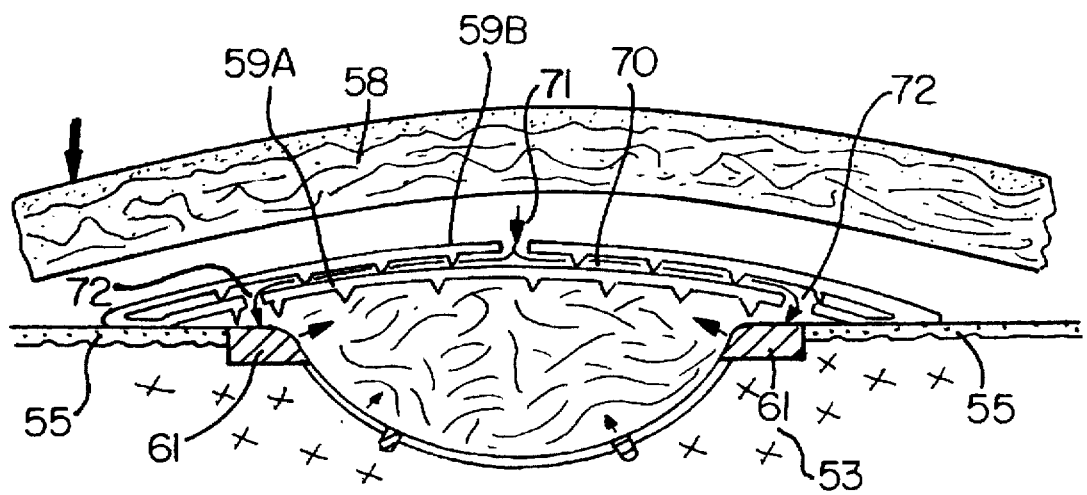
FIG. 42 is a cross-sectional view of the same bone defect as in FIGS. 36 to 39, covered by a further embodiment of the present invention.
Figure 43:
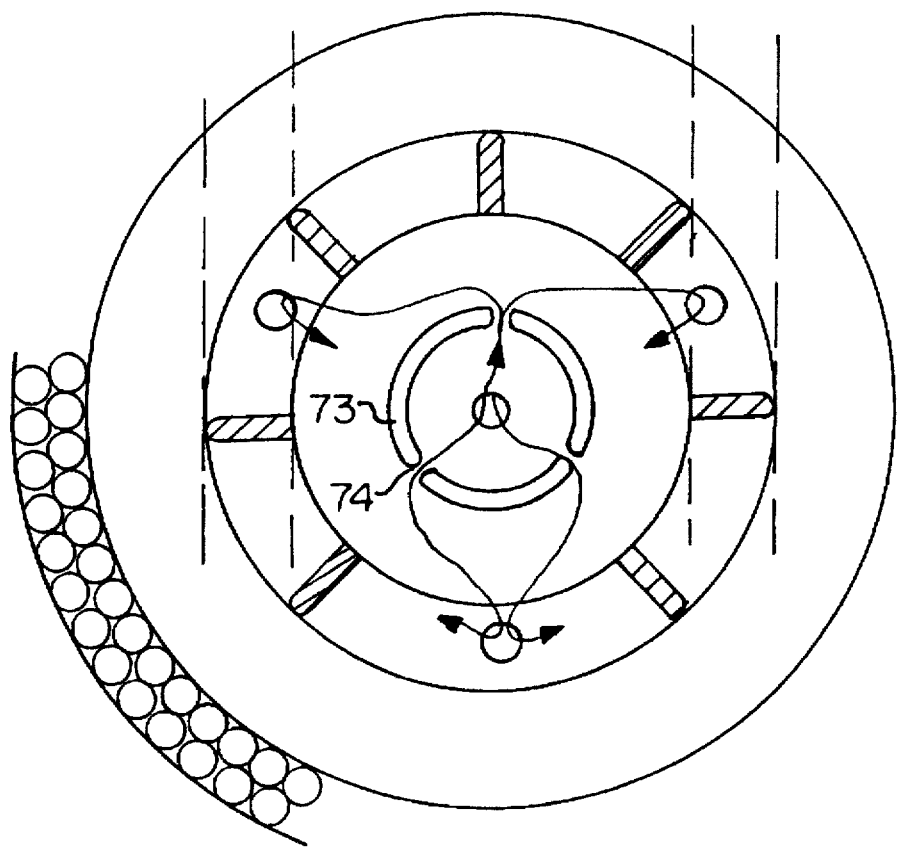
FIG. 43 is a horizontal cross-sectional view of the same defect as in FIG. 42.

FIGS. 42 and 43 show the same situation and views as FIGS. 38 and 39. The soft tissue flap 58 is replaced but is not yet in its final position. This embodiment of the element has two layers, 59A and 59B, instead of one as in FIGS. 38 and 39. The fact that both layers are provided with protrusions, means that the size and location of such protrusions regulate not only the space between the inner layer and the bone, but also the space 70 between the outer and inner layers. In addition, both the outer and the inner layer are perforated with at least one perforation, preferably, not larger that 100 µm.

There are at least two reasons why the element, preferably, should be provided with perforations. First, there are indications that transport of body fluids from the soft tissues to the hard (bone) tissues and vice versa is of benefit both for the soft and hard tissue nutrition and, thus, for the rate, safety, and predictability of the healing process. Second, the perforations allow ingrowth of tissue into the element, which stabilizes not only the element, but also the tissue flap in the intended position. This in turn counteracts the risk of rupture of the suture line or the flap tissue. Thus, the healing procedure is facilitated. In the embodiment shown in FIGS. 42 and 43, the location of the perforation or perforations of the outer layer is within the center of the element as indicated at 71, i.e., close to, or, preferably, quite above the holes or slots in the bone lateral to the defect. This means that the transport of body fluids between the soft and hard tissue compartments is maintained during the entire wound healing phase at the same time that the migration of continuous cell populations from the connective tissue to the bone defect is substantially delayed due to the long distance from the first connective tissue cell entrance 71 to the entrance into the bone defect 72. The central importance of the lateral perforations 61 is now obvious not only when the bone defect is occupied by an implant but in any situation, because the delivery of bone cells from these perforations means that the bone matrix front advancing toward the defect center already has passed and blocked the peripherally-located perforations of the inner element layer for connective tissue cells. As is shown in FIG. 42, the protrusions can be arranged in a continuous circumferent order as indicated at 73, resulting in a complete compartmentalization of the central perforations of the outer layer subject to one or more perforations 74 through this continuous beam. This arrangement further markedly delays the ingrowth of connective tissue cells into the bone defect, thereby increasing the chance for predictable guided bone regeneration.

Figure 44:
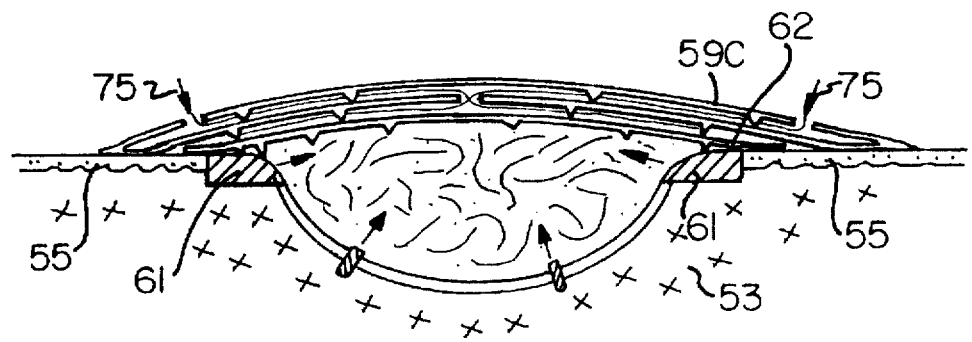
FIG. 44 is a cross-sectional view of the same bone defect as described above, with the element covering the defect having three layers.
Figure 45:
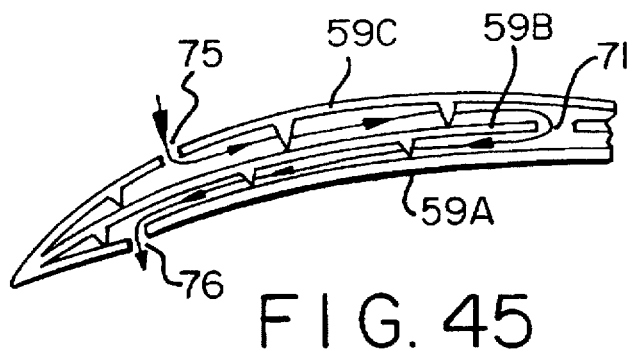
FIG. 45 is an enlarged fragmentary cross-sectional view of the left part of the element in FIG. 44.
Figure 46:
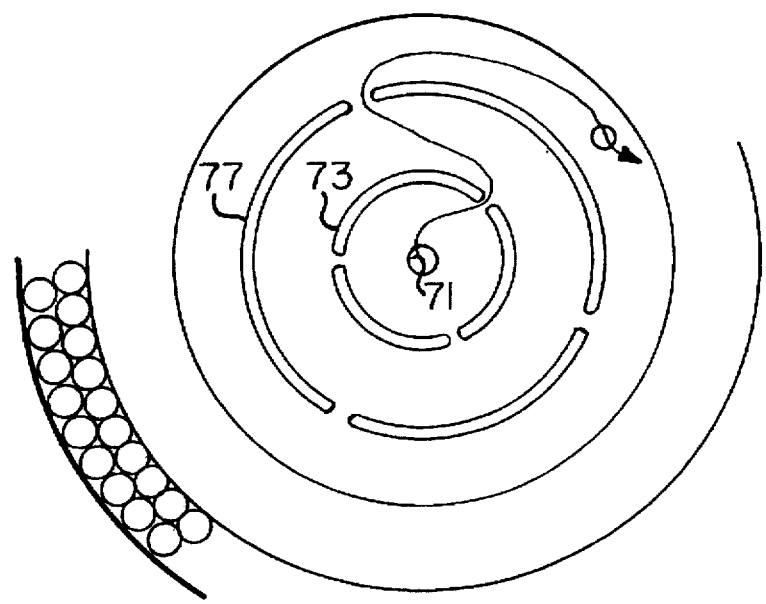
FIG. 46 is a plan view of the defect in FIG. 44.

A further embodiment of the element is shown in FIGS. 44 to 46. It can be seen that a third element layer 59C has been added, the outermost layer 59C having lateral perforations 75, while the middle layer 59B has a central perforation 71, and the innermost layer 59A has lateral perforations 76. Thus, the distance for cell migration is further increased. As is shown in FIG. 46, also the arrangement of another circumferent protrusion 77 may help to further delay the connective tissue cell migration.

In summary, embodiments of the invention adapted for selectively-guided tissue regeneration in the treatment of a cavity defect in a bone are depicted in FIGS. 36-46. The bone defect comprises an inner wall defined by spongious bone tissue and overlying healthy cortical bone tissue, with the defect having a lip defined by the overlying healthy outer cortical bone tissue. The lip has had cut into it surgically a plurality of cortical bone perforations extending outwardly from the lip and radially inwards through the overlying cortical bone tissue into the spongious bone tissue.

The article comprises a first layer having an inner surface, an outer surface, and a peripheral edge, with the inner surface being adapted to extend outwardly beyond the defect. It is also adapted to be disposed tightly adjacent healthy cortical bone tissue over a first zone that is peripheral to such cortical bone perforations, thereby enabling the minimizing of the growth of connective tissue inwardly into the space formed under the inner surface of the first portion and within the first zone.

The first layer further comprises a plurality of first short spacing members extending radially inward from the inner surface of the first layer. These are adapted to contact at spaced locations a borderline area of cortical bone tissue, which borderline area is defined by such lip and by being positioned inwardly from the first zone.

The article may also comprise at least one elongated protrusion having a free-end extending inwardly from the inner surface of the first layer, with the free-end being adapted to be in contact with the inner wall of the bone defect.

The first layer may further comprise an additional area comprising a plurality of peripheral perforations. Such an additional area borders the peripheral edge of the first layer and is located outwardly from such zone. The peripheral perforations collectively comprise a majority of the additional area of the first layer, thereby permitting radially inward growth through the peripheral perforations of soft tissue into contact with cortical bone tissue.

The article may also be employed with a defect that is occupied by a bone implant having an outer surface extending at least in part outwardly from the defect. In such a situation, the inner surface of the first layer is shaped to be disposed adjacent to but spaced from the outer surface of the implant extending beyond the defect. In this embodiment, at least one of the first short spacing members is adapted to be in contact with the outer surface of the implant, thereby creating a space into which new bone tissue may grow.

The article may also be made with two or three layers. In a two-layer embodiment, the first layer comprises at least two tissue-entrance perforations, and is adapted to be disposed in relation to the cortical bone perforations whereby such tissue-entrance perforations in the first layer are disposed outwardly above the cortical bone perforations. The second layer also has a peripheral edge and is located adjacent to but spaced from the outer surface of the first layer, with the second layer having an inner surface facing towards the defect and also facing the outer surface of the first layer. The inner surface of the second layer comprises at least one second layer spacing member having a free end adapted to be in contact with the outer surface of the first layer, thereby creating and maintaining a space between the inner surface of the second layer and the outer surface of the first layer. The second layer also comprises at least one connective tissue cell entrance perforation, whereby overlying connective tissue may grow through such connective tissue cell entrance perforation into the space between the second layer and the first layer.

A three-layer article comprises a third layer that is located adjacent to but spaced apart from the second layer, with its inner surface facing towards the defect and also towards the outer surface of the second layer. The inner surface of the third layer comprises at least one third layer spacing member having a free end adapted to be in contact with the outer surface of the second layer, thereby creating and maintaining a third space located between the inner surface of the third layer and the outer surface of the second layer. The third layer also comprises at least one connective tissue cell entrance perforation, which perforation is located distantly from a cell entrance perforation of the second layer, whereby overlying connective cell tissue may grow into such third space.

The article may be biodegradable and/or comprise at least one biofunctional substance.

The invention also comprises a method of providing selective influence on tissue regeneration in the vicinity of a bone defect, which method comprises the steps of (a) separating soft tissue from at least a portion of the surface of the bone defect, which portion is located adjacent the defect, and (b) disposing at such surface an embodiment of the article described above.

Thus, it is possible, within a broad range, to influence the rate of ingrowth of different cell types into a wound area aimed for guided tissue regeneration by varying: the placement of element layers in relation to the defect, the space between the layers, and the size and location of layer perforations.

The element of the present invention can be constructed in ways other than those described with reference to the drawings. It is also possible to provide elements of any type with active substances of the kind referred to herein.

In order to further illustrate the present invention, reference is made to the following examples of the preferred embodiment, based on experiences from guided tissue regeneration procedures (GTR-procedures).

EXAMPLE 1

Following mucoperiosteal flap elevation, recession-type defects (72 teeth) and interproximal defects (24 teeth; 40 defects) were created in 12 monkeys (Macaca Fascicularis). At each of the experimental sites, an element according to FIG. 23, having protrusions 33 with a length of 200 μm, perforations 37 with a diameter of 300 μm, protrusions 33A with a length of 200 μm, and perforations 37A with a diameter of 70 μm, was placed to cover the defect. The flaps were then repositioned and sutured to complete coverage of the element.

After a healing period of 1, 3, 6, and 12 months, the animals were sacrificed and the experimental teeth were dissected free and placed in 10 percent buffered formalin. The specimens were decalcified and embedded in paraffin. Buccolingual sections (recession-type defects) and mesiodistal sections (interproximal defects) of each root were prepared with a microtome set at 3-5 μm, stained with Haematoxylin-eosin or Mallory's connective tissue stain, and subjected to analysis in a light microscope.

Around all teeth, healing occurred with minimal gingival inflammation and recession. Element exposure was observed at 5 of the 72 recession-type defects and at 4 of the 40 interproximal defects. No element was rejected during the healing period, which varied from 1 to 12 months.

1-month histological observation: The element was completely integrated with the soft tissue of the gingiva, and connective tissue fibers were seen penetrating into the matrix. The apical extension of epithelial downgrowth terminated coronal to the border of the element and no epithelial cells were seen along the element. No inflammatory cell infiltrates were present, however, solitary macrophages and multinuclear foreign body giant cells were observed adjacent to the element material. New attachment had formed to a level corresponding to the coronal margin of the element.

3-month histological observation: New attachment was present along the entire root portion covered by the element. At this time, point bone regeneration was more pronounced. In some specimens, new bone had formed also within the element, thus, illustrating the biocompatiblity of the element material. Functionally-oriented periodontal ligament fibers were seen extending from the newly formed cementum to the newly formed bone and the adjacent gingival connective tissue. Overt signs of element fragmentation were seen in all specimens. As in the 1-month observation, only solitary inflammatory cells were seen adjacent to the element material.

6 and 12- month histological observation: Extensive amounts of new attachment and new bone had formed. No element material was seen, indicating complete degradation of the element.

It can be concluded that:
- the use of the element of the present invention in GTR-procedures resulted in extensive formation of new attachment and new bone;
- the integration of the element with the soft tissue flap during the initial healing minimized epithelial downgrowth, gingival recession, and element exposure; and
- the element was completely degraded within 6 to 12 months after surgery.

EXAMPLE 2

The study comprised 32 defects (12 furcational and 20 intrabony defects) in 28 patients referred to specialists in periodontology for the treatment of advanced periodontal disease. All patients participated in the study on a voluntary basis. Following the initial examination and informed consent, each patient was given detailed instruction in plaque control measures.

Following flap elevation, sealing, root planing and removal of granulation tissue, a biodegradable element, as that in Example 1, was adjusted to cover the defect. The coronal portion of the element was tightly adapted to the tooth-neck by a degradable sling suture. The flaps were repositioned and secured with interdental sutures to complete coverage of the element. Sutures were removed after 2 weeks. Following surgery, the patients were instructed not to perform mechanical plaque control at the surgical sites but to rinse the mouth with a 0.2% chlorhexidine digluconate solution (Hibitane$^R$, ICIPharma, Gothenburg, Sweden) twice daily for one minute. The mouth-rinse regimen was continued for 4 to 6 weeks. Self-performed mechanical plaque control was reinitiated 3 to 4 weeks after surgery. During the period of 3 months after surgery, the patients were maintained on a plaque control program which included professional tooth cleaning once every 2 weeks. During the subsequent 3 month period, the patients were recalled for the same plaque control program once every 4 weeks. No subgingival instrumentation was performed at any recall visit.

At the day of surgery, and 6 months after surgery, the following variables were assessed:

1. Gingival position: The distance from gingival margin to CEJ.
2. Probing pocket depth (PPD).
3. Probing attachment level vertically (PAL-V) using CEJ or other landmarks on the tooth as reference points.
4. Probing attachment level horizontally (PAL-H) for furcational defects.

Measurements were performed using a 1 mm calibrated probe (0.5 mm) and recorded to the nearest mm.

The results are summarized in Table 1 (furcational defects), and Table 2 (intrabony defects), below.

TABLE 1

CLINICAL ASSESSMENTS OF 12 TREATED FURCATION
DEGREE II DEFECTS IN 10 PATIENTS
6-Month Evaluation

| | Patient | Sex | Age | Tooth | PPD Initial (mm) | PPD Residual (mm) | PAL-V Gain (mm) | PAL-H Gain (mm) | Furcation at 6 Months | Position of Gingival Margin* (mm) |
|---|---|---|---|---|---|---|---|---|---|---|
| 1 | U.L. | Male | 41 | 48b | 5 | 3 | 2 | 2 | Closed | 0 |
| 2 | U.L. | | | 47b | 9 | 3 | 5 | 4 | Closed | −1 |
| 3 | G.S. | Female | 44 | 26b | 6 | 4 | 3 | 4 | Closed | 1 |
| 4 | S.D. | Female | 38 | 46b | 5 | 4 | 2 | 2 | Degree I | 1 |
| 5 | S.D. | | | 47b | 4 | 4 | 1 | 2 | Degree I | 1 |
| 6 | R.S. | Male | 46 | 36b | 5 | 3 | 3 | 4 | Closed | 0 |
| 7 | U.L. | Male | 42 | 37b | 6 | 4 | 2 | 3 | Degree I | 0 |
| 8 | A.S. | Male | 58 | 47b | 6 | 3 | 3 | 3 | Degree I | 0 |
| 9 | G.A. | Male | 39 | 46l | 4 | 1 | 5 | 3 | Closed | 2 |
| 10 | R.N. | Male | 56 | 16m | 6 | 2 | 2 | 2 | Degree I | −2 |
| 11 | M.R. | Female | 47 | 37b | 6 | 2 | 4 | 4 | Closed | 0 |
| 12 | A.A. | Male | 36 | 17b | 9 | 3 | 6 | 4 | Closed | 0 |

TABLE 1-continued

CLINICAL ASSESSMENTS OF 12 TREATED FURCATION
DEGREE II DEFECTS IN 10 PATIENTS
6-Month Evaluation

| Patient | Sex | Age | Tooth | PPD Initial (mm) | PPD Residual (mm) | PAL-V Gain (mm) | PAL-H Gain (mm) | Furcation at 6 Months | Position of Gingival Margin* (mm) |
|---|---|---|---|---|---|---|---|---|---|
| mean | | 44.7 | | 5.9 | 3.0 | 3.2 | 3.1 | | 0.2 |
| SD | | 7.3 | | 1.6 | 1.0 | 1.5 | 0.9 | | 1.0 |

PPD = Probing Pocket Depth
PAL = Probing Attachment Level (V = Vertical; H = Horizontal)
SD = Standard Deviation
*Position of Gingival Margin in relation to Pre-surgical Level (neg. value = Recession)

TABLE 2

CLINICAL ASSESSMENTS OF 20 TREATED
INFRABONY DEFECTS IN 18 PATIENTS
6-Month Evaluation

| Patient | Sex | Age | Tooth | PPD Initial (mm) | PPD Residual (mm) | PAL Gain (mm) | Position of Gingival Margin* (mm) |
|---|---|---|---|---|---|---|---|
| 1 K-G.S. | Male | 45 | 13 | 6 | 1 | 6 | 1 |
| 2 G.B. | Male | 46 | 11 | 12 | 1 | 9 | -2 |
| 3 S.F. | Female | 54 | 33 | 12 | 1 | 9 | -2 |
| 4 S.A. | Male | 62 | 43 | 6 | 1 | 6 | 1 |
| 5 S.L. | Male | 65 | 13 | 9 | 5 | 4 | 0 |
| 6 S.L. | | | 21 | 9 | 2 | 5 | -2 |
| 7 B.L. | Male | 61 | 46 | 12 | 3 | 4 | -5 |
| 8 B.L. | | | 44 | 10 | 6 | 4 | 0 |
| 9 B.J. | Male | 72 | 13 | 6 | 4 | 0 | -2 |
| 10 A.P. | Female | 47 | 21 | 10 | 4 | 4 | -2 |
| 11 B.G. | Female | 57 | 43 | 9 | 3 | 4 | -2 |
| 12 A-C.H. | Female | 41 | 45 | 9 | 5 | 3 | -1 |
| 13 B.W. | Male | 51 | 23 | 12 | 6 | 5 | -1 |
| 14 K.J. | Female | 46 | 36 | 9 | 2 | 7 | 0 |
| 15 G-M.L. | Female | 49 | 36 | 6 | 3 | 3 | 0 |
| 16 K.J. | Male | 50 | 22 | 6 | 4 | 4 | 2 |
| 17 B-M.H. | Female | 42 | 17 | 6 | 4 | 5 | 3 |
| 18 S.J. | Male | 46 | 12 | 8 | 2 | 3 | -3 |
| 19 J.K. | Female | 34 | 26 | 12 | 1 | 7 | -4 |
| 20 B.S. | Male | 51 | 14 | 9 | 3 | 6 | 0 |
| mean | | 51.1 | | 8.9 | 3.1 | 4.9 | -1.0 |
| SD | | 9.4 | | 2.3 | 1.7 | 2.1 | 2.0 |

PPD = Probing Pocket Depth
PAL = Probing Attachment Level
SD = Standard Deviation
*Position of Gingival Margin in relation to Pre-surgical Level (neg. value = Recession)

At the furcational defects, mean PPD was reduced from 5.9 to 3.0 mm. The mean gain of PAL-V was 3.2 mm and the mean gain of PAL-H was 3.1 mm, resulting in complete closure of 7 of the 12 defects. The remaining 5 furcational defects were converted to degree I involvement. The position of the gingival margin was unchanged or coronal to the presurgical level at 10 of the 12 furcational defects. Gingival recession had occurred only at 2 furcational defects.

At the infrabony defects, mean PPD was reduced from 8.9 to 3.1 mm. The mean gain of PAL amounted to 4.9 mm. Mean gingival recession amounted to 1.0 mm. The position of the gingival margin was unchanged or coronal to the presurgical level at 9 of the 20 infrabony defects. The gingival recession of the remaining 11 defects was on the average 2.4 mm (range 1–5 mm).

Based on the results of this study, it is concluded that the use of the biodegradable element of the present invention in GTR-procedure will result in pronounced gain of attachment.

EXAMPLE 3

The study comprised 32 defects (12 furcational and 20 intrabony defects) in 28 patients referred to specialists in periodontology for the treatment of advanced periodontal disease. All patients participated in the study on a voluntary basis. Following the initial examination and informed consent, each patient was given detailed instruction in plaque control measures.

Following flap elevation, scaling, root planing, and removal of granulation tissue, a biodegradable element, as that in Example 1, was adjusted to cover the defect. The coronal portion of the device was tightly adapted to the tooth-neck by a biodegradable sling suture. The flaps were repositioned and secured with interdental sutures to complete coverage of the element. Sutures were removed after 2 weeks. Following surgery, the patients were instructed not to perform mechanical plaque control at the surgical sites but to rinse the mouth with a 0.2% chlorhexidine digluconate solution (Hibitane$^R$, ICIPharma, Gothenburg, Sweden) twice daily for one minute. The mouth-rinse regimen was continued for 4 to 6 weeks. Self-performed mechanical plaque control was re-initiated 3 to 4 weeks after surgery. During the period of 3 months after surgery, the patients were maintained on a plaque control program which included professional tooth cleaning once every 2 weeks. During the subsequent 3 month period, the patients were recalled for the same plaque control program once every 4 weeks. No subgingival instrumentation was performed at any recall visit.

The gingival position was assessed prior to, and 6 months after, surgery.

The following variables were recorded at 2 weeks, and at 1, 3 and 6 months after surgery:

1. Gingival condition, Index 0–3:

0=Healthy, non-inflamed soft tissue at the element covered area.

1=Inflamed gingival margin, but predominantly healthy soft tissue at the element covered area.

2=Soft tissue with general redness along the element covered area, but with no swelling and/or suppuration.

3=General redness, swelling and/or suppuration.

2. Exposure of element (mm) in apical direction. The results are summarized in Table 3 (furcational defects) and Table 4 (infrabony defects), below.

TABLE 3

CLINICAL ASSESSMENTS OF 12 TREATED FURCATION
DEGREE II DEFECTS IN 10 PATIENTS
6-Month Evaluation

| | Patient | Sex | Age | Tooth | PPD Initial (mm) | PPD Residual (mm) | PAL-V Gain (mm) | PAL-H Gain (mm) | Furcation at 6 Months | Position of Gingival Margin* (mm) |
|---|---|---|---|---|---|---|---|---|---|---|
| 1 | U.L. | Male | 41 | 48b | 5 | 3 | 2 | 2 | Closed | 0 |
| 2 | U.L. | | | 47b | 9 | 3 | 5 | 4 | Closed | −1 |
| 3 | G.S. | Female | 44 | 26b | 6 | 4 | 3 | 4 | Closed | 1 |
| 4 | S.D. | Female | 38 | 46b | 5 | 4 | 2 | 2 | Degree I | 1 |
| 5 | S.D. | | | 47b | 4 | 4 | 1 | 2 | Degree I | 1 |
| 6 | R.S. | Male | 46 | 36b | 5 | 3 | 3 | 4 | Closed | 0 |
| 7 | U.L. | Male | 42 | 37b | 6 | 4 | 2 | 3 | Degree I | 0 |
| 8 | A.S. | Male | 58 | 47b | 6 | 3 | 3 | 3 | Degree I | 0 |
| 9 | G.A. | Male | 39 | 46l | 4 | 1 | 5 | 3 | Closed | 2 |
| 10 | R.N. | Male | 56 | 16m | 6 | 2 | 2 | 2 | Degree I | −2 |
| 11 | M.R. | Female | 47 | 37b | 6 | 2 | 4 | 4 | Closed | 0 |
| 12 | A.A. | Male | 36 | 17b | 9 | 3 | 6 | 4 | Closed | 0 |
| | mean | | 44.7 | | 5.9 | 3.0 | 3.2 | 3.1 | | 0.2 |
| | SD | | 7.3 | | 1.6 | 1.0 | 1.5 | 0.9 | | 1.0 |

PPD = Probing Pocket Depth
PAL = Probing Attachment Level (V = Vertical; H = Horizontal)
SD = Standard Deviation
*Position of Gingival Margin in relatio to Pre-surgical Level (neg. value = Recession)

TABLE 4

CLINICAL ASSESSMENTS OF 20
TREATED INFRABONY DEFECTS IN 18 PATIENTS
6-Month Evaluation

| | Patient | Sex | Age | Tooth | Gingival Condition Index (0–3) | | | | Exposure of Device (mm) | | | | Position of Gingival Margin* (mm) |
|---|---|---|---|---|---|---|---|---|---|---|---|---|---|
| | | | | | 2w | 1m | 3m | 6m | 2w | 1m | 3m | 6m | |
| 1 | K-G.S. | Male | 45 | 13 | 2 | 2 | 0 | 0 | 0 | 0 | 0 | 0 | 1 |
| 2 | G.B. | Male | 46 | 11 | 0 | 0 | 0 | 0 | 0 | 0 | 0 | 0 | −2 |
| 3 | S.F. | Female | 54 | 33 | 0 | 0 | 0 | 0 | 2 | 0 | 0 | 0 | −2 |
| 4 | S.A. | Male | 62 | 43 | 0 | 0 | 0 | 0 | 0 | 0 | 0 | 0 | 1 |
| 5 | S.L. | Male | 65 | 13 | 0 | 0 | 0 | 0 | 0 | 0 | 0 | 0 | 0 |
| 6 | S.L. | | | 21 | 0 | 0 | 0 | 0 | 0 | 0 | 0 | 0 | −2 |
| 7 | B.L. | Male | 61 | 46 | 0 | 0 | 0 | 0 | 2 | 2 | 0 | 0 | −5 |
| 8 | B.L. | | | 44 | 0 | 0 | 0 | 0 | 0 | 0 | 0 | 0 | 0 |
| 9 | B.J. | Male | 72 | 13 | 0 | 0 | 0 | 0 | 0 | 0 | 0 | 0 | −2 |
| 10 | A.P. | Female | 47 | 21 | 0 | 0 | 0 | 0 | 0 | 0 | 0 | 0 | −2 |
| 11 | B.G. | Female | 57 | 43 | 1 | 1 | 0 | 0 | 1 | 1 | 0 | 0 | −2 |
| 12 | A-C.H. | Female | 41 | 45 | 0 | 0 | 0 | 0 | 0 | 0 | 0 | 0 | −1 |
| 13 | B.W. | Male | 51 | 23 | 0 | 0 | 0 | 0 | 0 | 0 | 0 | 0 | −1 |
| 14 | K.J. | Female | 46 | 36 | 0 | 0 | 0 | 0 | 0 | 0 | 0 | 0 | 0 |
| 15 | G-M.L. | Female | 49 | 36 | 0 | 0 | 0 | 0 | 0 | 0 | 0 | 0 | 0 |
| 16 | K.J. | Male | 50 | 22 | 0 | 0 | 0 | 0 | 0 | 0 | 0 | 0 | 2 |
| 17 | B-M.H. | Female | 42 | 17 | 0 | 0 | 0 | 0 | 0 | 0 | 0 | 3 | |
| 18 | S.J. | Male | 46 | 12 | 0 | 0 | 0 | 0 | 0 | 0 | 0 | 0 | −3 |
| 19 | J.K. | Female | 34 | 26 | 0 | 0 | 0 | 0 | 0 | 0 | 0 | 0 | −4 |
| 20 | B.S. | Male | 51 | 14 | 0 | 0 | 0 | 0 | 0 | 0 | 0 | 0 | 0 |
| | mean | | 51.1 | | | | | | | | | | −1.0 |
| | SD | | 9.4 | | | | | | | | | | −1.0 |
| | Range | | 34–72 | | | | | | | | | | −5–3 |

SD = Standard Deviation; W = Weeks; M = Months
*Postition of Gingival Margin in Relation to Pre-surgical Level (neg. value = Recession)

Clinical signs of inflammation (Index 2) in the soft tissue covering the element was found adjacent to only 1 defect and was limited to the first month of healing. The position of the gingival margin was unchanged or coronal to the presurgical level at 10 of the 12 furcational defects and at 9 of the 20 intrabony defects. The gingival recession of the remaining 13 defects was on the average 2.2 mm (range 1–5 mm). Element exposure occurred at 5 of the 32 defects.

The very low incidence of gingival pathology, gingival recession, and element exposure, illustrates the biocompatibility and safety of the element of the present invention.

I claim:

1. An article adapted for selectively-guided tissue regeneration in the treatment of a periodontal defect adjacent to the root of a tooth, said article comprising
   (a) an element comprising a first sheet portion and a second sheet portion, said first portion having a first surface adapted to face towards said root, and having an outer surface, said first portion being adapted to be disposed adjacent said root at the site of said defect, said first portion having a coronal end and an apical end;
   (b) said second portion having an inner surface and an outer surface, said inner surface being opposite and essentially parallel to said outer surface of said first portion;
   (c) at least one of said portions comprising a plurality of perforations;
   (d) said element further comprising first spacing means located between said outer surface of said first portion and said inner surface of said second portion, said first spacing means being adapted to maintain said first portion and said second portion in essentially parallel relationship, thereby creating a first space, said first space being adapted to permit ingrowth of new connective tissue thereinto through said perforations; and
   (e) said element further comprising second spacing means, said second spacing means being adapted to create and maintain a second space between said root and said first surface, said second space having sufficient width perpendicular to the longitudinal axis of said root to permit ingrowth into said second space of periodontal ligament tissue.

2. The article of claim 1 further comprising tightly applying means adapted to permit the coronal end of said inner surface to be tightly applied to the surface of said root.

3. The article of claim 2, wherein said tightly applying means comprises a hollow channel extending across the width of said first portion near its coronal end, said channel having an outer boundary and being adapted to have disposed therein an anchoring ligature, said ligature being adapted when under tension to compress said inner surface tightly against the surface of said root.

4. The article of claim 3, wherein said ligature is displaceable longitudinally in said channel.

5. The article of claim 1, wherein said first portion has a variable stiffness.

6. The article of claim 1, wherein said second portion has a variable stiffness.

7. The article of claim 1, wherein said first spacing means comprises spacers having the shape of a truncated cone.

8. The article of claim 1, wherein said second spacing means comprises second spacers having a rectangular ross-section.

9. The article of claim 8, wherein said second spacers are located in a uniform pattern.

10. The article of claim 1, wherein said second spacing means comprises second spacers having a rectangular cross-section, and said first spacing means comprises first spacers having the shape of a truncated cone.

11. The article of claim 10, wherein a majority of said first spacers and said second spacers are centered opposite one another.

12. The article of claim 1, wherein said perforations are in said second portion and are rectangular.

13. The article of claim 1 wherein both of said portions have a plurality of perforations.

14. The article of claim 13, wherein the perforations in said first portion are circular.

15. The article of claim 13, wherein the cross-sectional area of individual perforations in said first portion is uniform and smaller than the cross-sectional area of individual perforations in said second portion.

16. The article of claim 1, wherein said first portion and said second portion are integral.

17. The article of claim 3, wherein said first spacing means comprises first spacing members having the shape of a truncated cone, and at least one of said first spacing members comprises a portion of said boundary of said hollow channel.

18. The article of claim 3, wherein said first portion further comprises a rib extending longitudinally across the width of said inner surface of said first portion near the coronal end thereof, and said rib defining a portion of said outer boundary of said hollow channel.

19. The article of claim 3 wherein the coronal end of said first surface further comprises a rib extending across the width of said first surface, said rib being adapted to be, in use, positioned against the surface of said root slightly apical to the cervix of said tooth.

20. The article of claim 19, wherein said rib is continuous.

21. The article of claim 1, wherein said element is biodegradable.

22. The article of claim 1, wherein said further element comprises at least one biofunctional substance.

23. A method of providing selective influence on tissue regeneration in the vicinity of a periodontal defect, said method comprising the steps of
   (a) separating soft tissue from at least a portion of the surface of a root of a tooth located at said defect, said portion comprising that area of said root surface located adjacent said defect; and
   (b) affixing to said root surface an article as defined in claim 1, said article being affixed near or slightly apical to the cervix of said root, and tightly affixing said article to prevent the growth in an apical direction of soft tissue along said root surface.

24. An article adapted for selectively-guided tissue regeneration in the treatment of a periodontal defect adjacent to the root of a tooth, said article comprising: an element comprising a first sheet portion and a second sheet portion, said first sheet portion having a first surface adapted to face towards said root, and having an outer surface, said first sheet portion being adapted to be disposed adjacent said root at the site of said defect, said first portion having a coronal and an apical end; said second sheet portion having an inner surface and an outer surface, said inner surface being opposite and essentially parallel to said outer surface of said first sheet portion; at least one of said portions comprising a plurality of perforations; said element further comprising a plurality of first spacers located between said outer surface of said first sheet portion and said inner surface of said second sheet portion, said first spacers being adapted to maintain said first sheet portion and said second sheet portion in essentially parallel relationship, thereby creating a first space, said first space being adapted to permit ingrowth of new connective tissue thereunto through said perforations; and said element further comprising a plurality of second spacers affixed to said inner surface of said first sheet portion and adapted to create and maintain a second space between said root and said first surface, said second space having sufficient width perpendicular to the longitudinal axis of said root to permit ingrowth into said second space of periodontal ligament tissue.

25. The article of claim 24, wherein at least a portion of said first spacers are affixed to or integral with said outer surface of said first sheet portion.

26. The article of claim 24 wherein the length and/or the cross-sectional area of individual members of said first spacers differ from the length and/or cross-sectional area of individual members of said second spacers.

* * * * *